(12) United States Patent
Blanchard et al.

(10) Patent No.: US 11,040,176 B2
(45) Date of Patent: Jun. 22, 2021

(54) CATHETER PLACEMENT DEVICE INCLUDING AN EXTENSIBLE NEEDLE SAFETY COMPONENT

(71) Applicant: C. R. Bard, Inc., Murray Hill, NJ (US)

(72) Inventors: Daniel B. Blanchard, Bountiful, UT (US); Huy Ngoc Tran, Riverton, UT (US); Rex A. Ribelin, Midvale, UT (US); Thomas S. Russell, Sandy, UT (US); Amir Orome, Sandy, UT (US); Jordan P. Diamond, Salt Lake City, UT (US); Eric W. Lindekugel, Salt Lake City, UT (US); Mark A. Christensen, Salt Lake City, UT (US); Jay A. Muse, Salt Lake City, UT (US)

(73) Assignee: C. R. Bard, Inc., Franklin Lakes, NJ (US)

(*) Notice: Subject to any disclaimer, the term of this patent is extended or adjusted under 35 U.S.C. 154(b) by 1134 days.

(21) Appl. No.: 15/154,384

(22) Filed: May 13, 2016

(65) Prior Publication Data

US 2016/0331938 A1    Nov. 17, 2016

Related U.S. Application Data

(60) Provisional application No. 62/162,548, filed on May 15, 2015.

(51) Int. Cl.
   *A61M 25/06* (2006.01)

(52) U.S. Cl.
   CPC .... *A61M 25/0606* (2013.01); *A61M 25/0618* (2013.01); *A61M 25/0693* (2013.01); *A61M 2205/586* (2013.01)

(58) Field of Classification Search
   CPC .......... A61M 25/0606; A61M 25/0618; A61M 25/0693; A61M 2205/586

(Continued)

(56) References Cited

U.S. PATENT DOCUMENTS

| 2,211,975 A | 8/1940 | Hendrickson |
| 2,259,488 A | 10/1941 | Raiche |

(Continued)

FOREIGN PATENT DOCUMENTS

| AU | 691141 B2 | 5/1998 |
| AU | 710967 B2 | 9/1999 |

(Continued)

OTHER PUBLICATIONS

EP 12782187.4 filed Sep. 10, 2013 Office Action dated Nov. 28, 2018.

(Continued)

*Primary Examiner* — Phillip A Gray
(74) *Attorney, Agent, or Firm* — Rutan & Tucker LLP

(57) ABSTRACT

An insertion device for inserting a catheter into a patient's body is disclosed. The insertion device combines needle insertion, guidewire advancement, catheter insertion, and needle shielding in a single device. In one embodiment, the insertion device comprises a housing including a hollow needle distally extending from the housing. At least a portion of the catheter is pre-disposed over the needle such that the catheter is disposed substantially external to the housing. A guidewire is included, as well as an advancement assembly that is configured to selectively advance the distal end of the guidewire out a distal opening of the needle in preparation for distal advancement of the catheter. The advancement assembly is further configured to enable distal catheter advancement before shielding the needle after use. The insertion device is configured to be grasped and used by a single hand of a user during advancement of the guidewire and the catheter.

39 Claims, 30 Drawing Sheets

(58) Field of Classification Search
USPC .................................................. 604/164.13
See application file for complete search history.

(56) References Cited

U.S. PATENT DOCUMENTS

| | | |
|---|---|---|
| 2,330,400 A | 9/1943 | Winder |
| D138,589 S | 8/1944 | Brandenburg |
| 3,185,151 A | 5/1965 | Czomy |
| 3,297,030 A | 1/1967 | Czomy et al. |
| 3,416,567 A | 12/1968 | von Dardel et al. |
| 3,469,579 A | 9/1969 | Hubert |
| 3,500,828 A | 3/1970 | Podhora |
| 3,552,384 A | 1/1971 | Pierie et al. |
| 3,572,334 A | 3/1971 | Petterson |
| 3,585,996 A | 6/1971 | Reynolds et al. |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,456,017 A | 6/1984 | Miles |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vailancourt |
| 4,525,157 A | 6/1985 | Vaillancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillari |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,850,961 A | 7/1989 | Wanderer et al. |
| 4,860,757 A | 8/1989 | Lynch et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,668 A | 4/1990 | Haindl et al. |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Raining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A | 10/1991 | Chuttani et al. |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleischhacker et al. |
| 5,098,395 A | 3/1992 | Fields |
| 5,098,396 A | 3/1992 | Taylor et al. |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |
| 5,156,590 A | 10/1992 | Vilmar |
| 5,156,596 A | 10/1992 | Balbierz et al. |
| 5,158,544 A | 10/1992 | Weinstein |
| 5,167,637 A | 12/1992 | Okada |
| 5,176,650 A | 1/1993 | Haining |
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa et al. |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |
| 5,246,426 A | 9/1993 | Lewis et al. |
| 5,246,430 A | 9/1993 | MacFarlane |

(56) References Cited

U.S. PATENT DOCUMENTS

| | | |
|---|---|---|
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Honing |
| 5,423,760 A | 6/1995 | Yoon |
| 5,425,718 A | 6/1995 | Tay et al. |
| 5,431,506 A | 7/1995 | Masunaga |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge et al. |
| 5,542,933 A | 8/1996 | Marks |
| 5,554,136 A | 9/1996 | Luther |
| 5,562,629 A | 10/1996 | Naughton et al. |
| 5,562,630 A | 10/1996 | Nichols |
| 5,562,631 A | 10/1996 | Bogert |
| 5,562,633 A | 10/1996 | Wozencroft |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,575,777 A | 11/1996 | Cover et al. |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Klakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,700,250 A | 12/1997 | Erskine |
| 5,702,367 A | 12/1997 | Cover et al. |
| 5,702,369 A | 12/1997 | Mercereau |
| 5,704,914 A | 1/1998 | Stocking et al. |
| 5,722,425 A | 3/1998 | Bostrom |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes |
| 5,749,371 A | 5/1998 | Zadini et al. |
| 5,749,857 A | 5/1998 | Cuppy |
| 5,749,861 A | 5/1998 | Guala et al. |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,835 A | 9/1998 | Ryan et al. |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Repine et al. |
| 5,843,002 A | 12/1998 | Pecor et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |

(56) References Cited

U.S. PATENT DOCUMENTS

| | | |
|---|---|---|
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| D413,382 S | 8/1999 | Maissami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther |
| 6,056,726 A | 5/2000 | Isaacson |
| 6,059,484 A | 5/2000 | Greive |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,109,264 A | 8/2000 | Sauer |
| 6,117,108 A | 9/2000 | Woehr et al. |
| 6,120,494 A | 9/2000 | Jonkman |
| 6,126,633 A | 10/2000 | Kaji et al. |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Green et al. |
| 6,221,048 B1 | 4/2001 | Phelps |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki et al. |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,607,511 B2 | 8/2003 | Halseth et al. |
| 6,616,630 B1 | 9/2003 | Woehr |
| 6,620,136 B1 | 9/2003 | Pressly, Sr. et al. |
| 6,623,449 B2 | 9/2003 | Paskar |
| 6,626,868 B1 | 9/2003 | Prestidge et al. |
| 6,626,869 B1 | 9/2003 | Bint |
| 6,629,959 B2 | 10/2003 | Kuracina et al. |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |

(56) References Cited

U.S. PATENT DOCUMENTS

| | | |
|---|---|---|
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,687 B2 | 6/2010 | Menzi et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,850,644 B2 | 12/2010 | Gonzalez et al. |
| 7,857,770 B2 | 12/2010 | Raulerson et al. |
| D634,843 S | 3/2011 | Kim et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |
| 7,972,324 B2 | 7/2011 | Quint |
| D643,531 S | 8/2011 | van der Weiden |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |

(56) References Cited

U.S. PATENT DOCUMENTS

| | | |
|---|---|---|
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,579,881 B2 | 11/2013 | Agro et al. |
| 8,585,651 B2 | 11/2013 | Asai |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,945,011 B2 | 2/2015 | Sheldon et al. |
| 8,951,230 B2 | 2/2015 | Tanabe et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,022,979 B2 | 5/2015 | Woehr |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,089,674 B2 | 7/2015 | Ginn et al. |
| 9,095,683 B2 | 8/2015 | Hall et al. |
| 9,101,746 B2 | 8/2015 | Stout et al. |
| 9,108,021 B2 | 8/2015 | Flyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |
| 9,162,037 B2 | 10/2015 | Belson et al. |
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |

(56) References Cited

U.S. PATENT DOCUMENTS

| | | |
|---|---|---|
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 | 6/2016 | Isaacson et al. |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| D775,330 S | 12/2016 | Blennow et al. |
| 9,522,254 B2 | 12/2016 | Belson |
| D776,259 S | 1/2017 | Eldredge |
| 9,545,495 B2 | 1/2017 | Goral et al. |
| 9,554,817 B2 | 1/2017 | Goldfarb et al. |
| D779,059 S | 2/2017 | Nino et al. |
| D779,661 S | 2/2017 | McKnight et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| D791,311 S | 7/2017 | Yantz |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| D810,282 S | 2/2018 | Ratjen |
| D815,737 S | 4/2018 | Bergstrom et al. |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 10,328,239 B2 | 6/2019 | Belson |
| 10,384,039 B2 | 8/2019 | Ribelin et al. |
| 10,426,931 B2 | 10/2019 | Blanchard et al. |
| D870,271 S | 12/2019 | Kheradpir et al. |
| D870,883 S | 12/2019 | Harding et al. |
| 10,493,262 B2 | 12/2019 | Tran et al. |
| 10,525,236 B2 | 1/2020 | Belson |
| 10,688,280 B2 | 6/2020 | Blanchard et al. |
| 10,688,281 B2 | 6/2020 | Blanchard et al. |
| 10,722,685 B2 | 7/2020 | Blanchard et al. |
| 10,806,906 B2 | 10/2020 | Warring et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |
| 2005/0027256 A1 | 2/2005 | Barker et al. |
| 2005/0033137 A1 | 2/2005 | Oral et al. |
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Raining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0079787 A1 | 4/2006 | Whiting et al. |
| 2006/0084964 A1 | 4/2006 | Knudson et al. |
| 2006/0150245 A1 | 7/2006 | Woehr |
| 2006/0161115 A1 | 7/2006 | Fangrow |
| 2006/0167405 A1 | 7/2006 | King et al. |
| 2006/0200080 A1 | 9/2006 | Abulhaj |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0255221 A1 | 11/2007 | Nakajima |
| 2007/0276288 A1 | 11/2007 | Khaw |
| 2008/0039796 A1 | 2/2008 | Nakajima |
| 2008/0065011 A1 | 3/2008 | Marchand et al. |
| 2008/0082082 A1 | 4/2008 | Carlyon et al. |
| 2008/0097330 A1 | 4/2008 | King et al. |
| 2008/0108911 A1 | 5/2008 | Palmer |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0018567 A1 | 1/2009 | Escudero et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |

(56) References Cited

U.S. PATENT DOCUMENTS

| | | |
|---|---|---|
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0016838 A1 | 1/2010 | Butts et al. |
| 2010/0036331 A1 | 2/2010 | Sen |
| 2010/0056910 A1 | 3/2010 | Yanuma |
| 2010/0057183 A1 | 3/2010 | Mangiardi et al. |
| 2010/0087787 A1 | 4/2010 | Woehr et al. |
| 2010/0094116 A1 | 4/2010 | Silverstein |
| 2010/0094310 A1 | 4/2010 | Warring et al. |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204660 A1 | 8/2010 | McKinnon et al. |
| 2010/0204675 A1 | 8/2010 | Woehr et al. |
| 2010/0210934 A1 | 8/2010 | Belson |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0071857 A1 | 3/2012 | Goldfarb et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kurrus et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0158506 A1 | 6/2013 | Harris et al. |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1 | 11/2013 | Burkholz et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0243734 A1 | 8/2014 | Eubanks et al. |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276432 A1 | 9/2014 | Bierman et al. |
| 2014/0276434 A1 | 9/2014 | Woehr et al. |
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 * | 2/2015 | Korkuch ........... A61M 25/0606 604/510 |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1 | 7/2015 | Teoh |
| 2015/0190617 A1 | 7/2015 | Anderson et al. |
| 2015/0202414 A1 | 7/2015 | Hwang |
| 2015/0202421 A1 | 7/2015 | Ma et al. |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |
| 2016/0106959 A1 | 4/2016 | Woehr |
| 2016/0114136 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2016/0175563 A1 | 6/2016 | Woehr et al. |
| 2016/0184557 A1 | 6/2016 | Call et al. |
| 2016/0199575 A1 | 7/2016 | Belley et al. |
| 2016/0206852 A1 | 7/2016 | Morgan et al. |
| 2016/0206858 A1 | 7/2016 | Ishida |
| 2016/0220161 A1 | 8/2016 | Goral et al. |
| 2016/0220786 A1 | 8/2016 | Mitchell et al. |
| 2016/0256667 A1 | 9/2016 | Ribelin et al. |
| 2016/0296729 A1 | 10/2016 | Fuchs et al. |
| 2016/0310704 A1 | 10/2016 | Ng et al. |
| 2016/0331937 A1 | 11/2016 | Teoh |
| 2016/0354580 A1 | 12/2016 | Teoh et al. |
| 2016/0361490 A1 | 12/2016 | Phang et al. |

(56) References Cited

U.S. PATENT DOCUMENTS

| | | |
|---|---|---|
| 2016/0361519 A1 | 12/2016 | Teoh et al. |
| 2017/0000982 A1 | 1/2017 | Ishida |
| 2017/0035992 A1 | 2/2017 | Harding et al. |
| 2017/0043132 A1 | 2/2017 | Ishida |
| 2017/0087338 A1 | 3/2017 | Belson |
| 2017/0136217 A1 | 5/2017 | Riesenberger et al. |
| 2017/0203050 A1 | 7/2017 | Bauer et al. |
| 2017/0209668 A1 | 7/2017 | Belson |
| 2017/0246429 A1 | 8/2017 | Tan et al. |
| 2017/0259036 A1 | 9/2017 | Belson |
| 2017/0361071 A1 | 12/2017 | Belson |
| 2018/0028780 A1 | 2/2018 | Blanchard et al. |
| 2018/0071509 A1 | 3/2018 | Tran et al. |
| 2018/0099123 A1 | 4/2018 | Woehr |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |
| 2019/0022358 A1 | 1/2019 | Belson |
| 2019/0192829 A1 | 6/2019 | Belson et al. |
| 2019/0201667 A1 | 7/2019 | Braithwaite et al. |
| 2019/0240459 A1 | 8/2019 | Belson |
| 2019/0275303 A1 | 9/2019 | Tran et al. |
| 2019/0307986 A1 | 10/2019 | Belson |
| 2019/0351193 A1 | 11/2019 | Hall |
| 2019/0351196 A1 | 11/2019 | Ribelin et al. |
| 2020/0001051 A1 | 1/2020 | Huang et al. |
| 2020/0094037 A1 | 3/2020 | Tran et al. |
| 2020/0261696 A1 | 8/2020 | Blanchard |
| 2020/0261703 A1 | 8/2020 | Belson et al. |
| 2020/0316347 A1 | 10/2020 | Belson |
| 2021/0052858 A1 | 2/2021 | Isaacson et al. |

FOREIGN PATENT DOCUMENTS

| | | |
|---|---|---|
| CN | 1178707 A | 4/1998 |
| CN | 1319023 A | 10/2001 |
| CN | 1523970 | 8/2004 |
| CN | 1871043 A | 11/2006 |
| CN | 101242868 A | 8/2008 |
| CN | 101293122 A | 10/2008 |
| CN | 101417159 A | 4/2009 |
| CN | 101784300 A | 7/2010 |
| CN | 102099075 A | 6/2011 |
| CN | 102939129 A | 2/2013 |
| CN | 104689456 A | 6/2015 |
| CN | 105073174 A | 11/2015 |
| CN | 105188826 A | 12/2015 |
| CN | 105705191 A | 6/2016 |
| DE | 20210394 U1 | 9/2002 |
| EP | 0314470 A2 | 5/1989 |
| EP | 417764 A1 | 3/1991 |
| EP | 475857 A1 | 3/1992 |
| EP | 515710 A1 | 12/1992 |
| EP | 567321 A2 | 10/1993 |
| EP | 652020 A2 | 5/1995 |
| EP | 747075 A2 | 12/1996 |
| EP | 750916 A2 | 1/1997 |
| EP | 778043 A1 | 6/1997 |
| EP | 800790 A2 | 10/1997 |
| EP | 832663 A2 | 4/1998 |
| EP | 910988 A1 | 4/1999 |
| EP | 942761 A1 | 9/1999 |
| EP | 1075850 A2 | 2/2001 |
| EP | 1378263 A2 | 1/2004 |
| EP | 1418971 A2 | 5/2004 |
| EP | 1457229 A1 | 9/2004 |
| EP | 1611916 A1 | 1/2006 |
| EP | 1907042 A2 | 4/2008 |
| EP | 2150304 A2 | 2/2010 |
| EP | 2272432 A1 | 1/2011 |
| EP | 2569046 A1 | 3/2013 |
| JP | 2003-159334 A | 6/2003 |
| JP | 2004-130074 A | 4/2004 |
| JP | 2004-223252 A | 8/2004 |
| JP | 2005-137888 A | 6/2005 |
| JP | 2009-500129 A | 1/2009 |
| JP | 2010-088521 A | 4/2010 |
| JP | 2013-529111 | 7/2013 |
| JP | 2018-118079 A | 8/2018 |
| WO | 83/01575 A1 | 5/1983 |
| WO | 1983001575 A1 | 5/1983 |
| WO | 1992013584 A1 | 8/1992 |
| WO | 92/22344 A1 | 12/1992 |
| WO | 1992022344 A1 | 12/1992 |
| WO | 1995011710 A1 | 5/1995 |
| WO | 95/19193 A1 | 7/1995 |
| WO | 1995019193 A1 | 7/1995 |
| WO | 95/23003 A1 | 8/1995 |
| WO | 1995023003 A1 | 8/1995 |
| WO | 96/32981 A1 | 10/1996 |
| WO | 1996032981 A1 | 10/1996 |
| WO | 1996040359 A1 | 12/1996 |
| WO | 97/05912 A2 | 2/1997 |
| WO | 1997005912 A2 | 2/1997 |
| WO | 97/21458 A1 | 6/1997 |
| WO | 1997021458 A1 | 6/1997 |
| WO | 1997045151 A1 | 12/1997 |
| WO | 98/24494 A1 | 6/1998 |
| WO | 1998024494 A1 | 6/1998 |
| WO | 1998030268 A1 | 7/1998 |
| WO | 1998053875 A1 | 12/1998 |
| WO | 1999008742 A1 | 2/1999 |
| WO | 1999026682 A1 | 6/1999 |
| WO | 00/06226 A1 | 2/2000 |
| WO | 00/12160 A1 | 3/2000 |
| WO | 2000012167 A1 | 3/2000 |
| WO | 00/47256 A1 | 8/2000 |
| WO | 2001007103 A1 | 2/2001 |
| WO | 01/26725 A1 | 4/2001 |
| WO | 2002041932 A2 | 5/2002 |
| WO | 02/066093 A2 | 8/2002 |
| WO | 03/11381 A1 | 2/2003 |
| WO | 03/43686 A1 | 5/2003 |
| WO | 03/043686 A1 | 5/2003 |
| WO | 03/47675 A2 | 6/2003 |
| WO | 03/047675 A2 | 6/2003 |
| WO | 2004/018031 A2 | 3/2004 |
| WO | 2004106203 A3 | 12/2004 |
| WO | 2005002659 A1 | 1/2005 |
| WO | 2005/074412 A2 | 8/2005 |
| WO | 2005/087306 A1 | 9/2005 |
| WO | 2006062996 A2 | 6/2006 |
| WO | 2007006055 A2 | 1/2007 |
| WO | 2007/032343 A1 | 3/2007 |
| WO | 2007094841 A1 | 8/2007 |
| WO | 2007098355 A1 | 8/2007 |
| WO | 2007098359 A1 | 8/2007 |
| WO | 2008005618 A2 | 1/2008 |
| WO | 2008030999 A2 | 3/2008 |
| WO | 2008/131300 A2 | 10/2008 |
| WO | 2008137956 A2 | 11/2008 |
| WO | 2009/001309 A1 | 12/2008 |
| WO | 2008147600 A1 | 12/2008 |
| WO | 2009031161 A1 | 3/2009 |
| WO | 2009114837 A2 | 9/2009 |
| WO | 2009/124990 A1 | 10/2009 |
| WO | 2010015676 A1 | 2/2010 |
| WO | 2010/048449 A2 | 4/2010 |
| WO | 2010/132608 A2 | 11/2010 |
| WO | 2011036574 A1 | 3/2011 |
| WO | 2011143621 A1 | 11/2011 |
| WO | 2012106266 A1 | 8/2012 |
| WO | 2012154277 A1 | 11/2012 |
| WO | 2012174109 A1 | 12/2012 |
| WO | 2013119557 A1 | 8/2013 |
| WO | 2013126446 A1 | 8/2013 |
| WO | 2013187827 A1 | 12/2013 |
| WO | 2014006403 A1 | 1/2014 |
| WO | 2014029424 A1 | 2/2014 |
| WO | 2014074417 A2 | 5/2014 |
| WO | 2014081942 A1 | 5/2014 |
| WO | 2014/123848 A1 | 8/2014 |
| WO | 2014120741 A1 | 8/2014 |

(56) References Cited

FOREIGN PATENT DOCUMENTS

| WO | 2014133617 A1 | 9/2014 |
|---|---|---|
| WO | 2014140257 A1 | 9/2014 |
| WO | 2014140265 A1 | 9/2014 |
| WO | 2014/165783 A1 | 10/2014 |
| WO | 2014158908 A1 | 10/2014 |
| WO | 2014182421 A1 | 11/2014 |
| WO | 2014197656 A1 | 12/2014 |
| WO | 2014204593 A1 | 12/2014 |
| WO | 2015017136 A1 | 2/2015 |
| WO | 2015024904 A1 | 2/2015 |
| WO | 2015035393 A1 | 3/2015 |
| WO | 2015058136 A1 | 4/2015 |
| WO | 15108913 A1 | 7/2015 |
| WO | 2015/168655 A2 | 11/2015 |
| WO | 15164912 A1 | 11/2015 |
| WO | 2016/037127 A1 | 3/2016 |
| WO | 16178974 A1 | 11/2016 |
| WO | 2018/049413 A1 | 3/2018 |
| WO | 2018170349 A1 | 9/2018 |
| WO | 2019173641 A1 | 9/2019 |

OTHER PUBLICATIONS

SG 11201709185X filed Nov. 8, 2017 Office Action dated Oct. 5, 2018.
SG 11201709193S filed Nov. 8, 2017 Office Action dated Oct. 5, 2018.
U.S. Appl. No. 14/846,387, filed Sep. 4, 2015 Notice of Allowance dated Oct. 29, 2018.
U.S. Appl. No. 14/866,441, filed Sep. 25, 2015 Notice of Allowance dated Oct. 17, 2018.
U.S. Appl. No. 15/154,808, filed May 13, 2016 Advisory Action dated Oct. 26, 2018.
U.S. Appl. No. 15/377,880, filed Dec. 13, 2016 Final Office Action dated Oct. 19, 2018.
U.S. Appl. No. 15/481,773, filed Apr. 7, 2017 Final Office Action dated Jan. 10, 2019.
U.S. Appl. No. 15/702,537, filed Sep. 12, 2017 Non-Final Office Action dated Nov. 29, 2018.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
U.S. Appl. No. 14/099,050, filed Dec. 6, 2013 Non-Final Office Action dated Dec. 22, 2015.
U.S. Appl. No. 14/099,050, filed Dec. 6, 2013 Non-Final Office Action dated Jul. 19, 2016.
U.S. Appl. No. 14/167,149, filed Jan. 29, 2014 Non-Final Office Action dated Oct. 21, 2015.
U.S. Appl. No. 14/167,149, filed Jan. 29, 2014 Notice of Allowance dated Jul. 6, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
U.S. Appl. No. 14/585,800, filed Dec. 30, 2014 Non-Final Office Action dated May 16, 2016.
U.S. Appl. No. 14/585,800, filed Dec. 30, 2014 Non-Final Office Action dated Oct. 8, 2015.
U.S. Appl. No. 14/866,441, filed Sep. 25, 2015 Final Office Action dated Sep. 23, 2016.
U.S. Appl. No. 14/866,441, filed Sep. 25, 2015 Non-Final Office Action dated Mar. 14, 2016.
U.S. Appl. No. 14/866,738, filed Sep. 25, 2015 Non-Final Office Action dated Oct. 31, 2016.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
EP 16797047.4 filed Dec. 6, 2017 Supplemental European Search Report dated Jan. 9, 2019.
JP 2016-563441 filed Oct. 19, 2016 Office Action dated Jan. 25, 2019.
U.S. Appl. No. 14/585,800, filed Dec. 30, 2014 Notice of Allowance dated Feb. 25, 2019.
U.S. Appl. No. 15/154,808, filed May 13, 2016 Notice of Allowance dated Apr. 16, 2019.
U.S. Appl. No. 151/02,537, filed Sep. 12, 2017 Final Office Action dated Mar. 8, 2019.
CA 2,799,360 filed May 13, 2011 Office Action dated Jun. 7, 2017.
CN 201380073657.4 filed Aug. 21, 2015 Office Action dated Jun. 28, 2017.
CN 201480019467.9 filed Sep. 29, 2015 Office Action dated Apr. 6, 2017.
CN 201510079782.7 filed Feb. 13, 2015 Office Action dated Dec. 30, 2016.
JP 2013-510353 filed Oct. 31, 2012 Office Action dated Dec. 15, 2016.
JP 2016-107046 filed May 30, 2016 Office Action dated Apr. 26, 2017.
U.S. Appl. No. 14/099,050, filed Dec. 6, 2013 Advisory Action dated Jun. 1, 2017.
U.S. Appl. No. 14/099,050, filed Dec. 6, 2013 Final Office Action dated Jan. 30, 2017.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/174,071, filed Feb. 6, 2014 Final Office Action dated Dec. 2, 2016.
U.S. Appl. No. 14/192,541, filed Feb. 27, 2014 Notice of Allowance dated Dec. 6, 2016.

(56) References Cited

OTHER PUBLICATIONS

U.S. Appl. No. 14/192,541, filed Feb. 27, 2014 Notice of Corrected Allowability dated Mar. 8, 2017.
U.S. Appl. No. 14/250,093, filed Apr. 10, 2014 Advisory Action dated May 19, 2017.
U.S. Appl. No. 14/250,093, filed Apr. 10, 2014 Final Office Action dated Mar. 9, 2017.
U.S. Appl. No. 14/250,093, filed Apr. 10, 2014 Non-Final Office Action dated Nov. 16, 2016.
U.S. Appl. No. 14/250,093, filed Apr. 10, 2014 Panel Decision dated Jul. 14, 2017.
U.S. Appl. No. 14/585,800, filed Dec. 30, 2014 Non-Final Office Action dated Nov. 29, 2016.
U.S. Appl. No. 14/585,800, filed Dec. 30, 2014 Notice of Allowance dated Jul. 3, 2017.
U.S. Appl. No. 14/702,580, filed May 1, 2015 Final Office Action dated Sep. 1, 2017.
U.S. Appl. No. 14/702,580, filed May 1, 2015 Non-Final Office Action dated May 3, 2017.
U.S. Appl. No. 14/750,658, filed Jun. 25, 2016 Non-Final Office Action dated Mar. 9, 2017.
U.S. Appl. No. 14/750,658, filed Jun. 25, 2016 Notice of Allowance dated Jul. 20, 2017.
U.S. Appl. No. 14/846,387, filed Sep. 4, 2015 Non-Final Office Action dated Sep. 22, 2017.
U.S. Appl. No. 14/866,441, filed Sep. 25, 2015 Advisory Action dated Dec. 22, 2016.
U.S. Appl. No. 14/866,441, filed Sep. 25, 2015 Non-Final Office Action dated Apr. 7, 2017.
U.S. Appl. No. 14/866,738, filed Sep. 25, 2015 Final Office Action dated Feb. 24, 2017.
U.S. Appl. No. 14/866,738, filed Sep. 25, 2015 Notice of Panel Decision dated Jun. 23, 2017.
U.S. Appl. No. 14/876,735, filed Oct. 6, 2015 Non-Final Office Action dated Mar. 30, 2017.
U.S. Appl. No. 29/536,043, filed Aug. 12, 2015 Non-Final Office Action dated Aug. 31, 2017.
U.S. Appl. No. 29/545,436, filed Nov. 12, 2015 Non-Final Office Action dated Sep. 12, 2017.
JP 2015-560173 filed Aug. 28, 2015 Office Action dated Aug. 2, 2018.
PCT/US2017/051214 filed Sep. 12, 2017 International Search Report and Written Opinion dated Nov. 13, 2017.
U.S. Appl. No. 15/154,808, filed May 13, 2016 Final Office Action dated Aug. 16, 2018.
U.S. Appl. No. 15/481,773, filed Apr. 7, 2017 Non-Final Office Action dated Jun. 29, 2018.
Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-Intima™ Integrated Safety IV Catheter Brochure, © 2001.
Becton Dickinson, Insyte® AutoGuard™ Shielded I.V. Catheter Brochure, 1998.
CN 201180029526.7 filed Dec. 14, 2012 First Office Action dated Apr. 21, 2014.
CN 201280008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
Cook Medical "Lunderquist Extra-Stiff wire guide" (2012).
Endovascular Today "Coiled Stainless Steel Guidewires" Buyer's Guide pp. 13-20, (2012).

EP 10075422.5 filed Jul. 5, 2008 European search report and written opinion dated Dec. 1, 2010.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 13876666.2 filed Sep. 7, 2015 Extended European Search Report dated Sep. 20, 2016.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
Hadaway, Lynn C., A Midline Alternative to Central and Peripheral Venous Access, Caring Magazine, May 1990, pp. 45-50.
International search report and written opinion dated Apr. 2, 2012 for PCT/US2012/023192.
International search report and written opinion dated Jun. 1, 2007 for PCT/US2006/026671.
International search report and written opinion dated Oct. 23, 2008 for PCT/US2007/068393.
JP 2013-510353 filed Oct. 31, 2012 First Office Action dated Feb. 19, 2015.
JP 2013-510353 filed Oct. 31, 2012 Second Office Action dated Jan. 28, 2016.
JP 2016-107046 filed May 30, 2016 Office Action dated Jul. 28, 2016.
Menlo Care, Landmark™ Aquavene® Catheters Brochure, 1992.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Publications on Aquavene® Technology, Aug. 1992.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
PCT/US15/28950 filed May 1, 2015 International Search Report and Written Opinion dated Oct. 19, 2015.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
CN 201380073657.4 filed Aug. 21, 2015 Office Action dated Mar. 2, 2018.
CN 201510079782.7 filed Feb. 13, 2015 Office Action dated Feb. 5, 2018.
CN 201510079782.7 filed Feb. 13, 2015 Office Action dated Sep. 19, 2017.
EP 07783404.2 filed Jan. 19, 2009 Office Action dated Mar. 7, 2018.

(56) References Cited

OTHER PUBLICATIONS

EP 11781384.0 filed Sep. 21, 2012 Extended European Search Report dated Oct. 31, 2017.
EP 12782187.4 filed Sep. 10, 2013 Office Action dated Apr. 24, 2018.
EP 15785819.2 filed Dec. 2, 2016 Extended European Search Report dated Dec. 4, 2017.
EP 16797029.2 filed Nov. 21, 2017 Extended European Search Report dated May 3, 2018.
JP 2015-560173 filed Aug. 28, 2015 Office Action dated Sep. 19, 2017.
JP 2016-107046 filed May 30, 2016 Office Action dated Nov. 7, 2017.
PCT/CN2017/075370 filed Mar. 1, 2017 International Search Report and Written Opinion dated Nov. 30, 2017.
RU 2017141812 filed Nov. 30, 2017 Office Action dated Jan. 31, 2018.
U.S. Appl. No. 14/250,093, filed Apr. 10, 2014 Examiner's Answer dated Jun. 20, 2018.
U.S. Appl. No. 14/250,093, filed Apr. 10, 2014 Final Office Action dated Nov. 6, 2017.
U.S. Appl. No. 14/585,800, filed Dec. 30, 2014 Final Office Action dated May 11, 2018.
U.S. Appl. No. 14/585,800, filed Dec. 30, 2014 Non-Final Office Action dated Nov. 3, 2017.
U.S. Appl. No. 14/702,580, filed May 1, 2015 Advisory Action dated Nov. 13, 2017.
U.S. Appl. No. 14/702,580, filed May 1, 2015 Notice of Allowance dated Dec. 8, 2017.
U.S. Appl. No. 14/846,387, filed Sep. 4, 2015 Advisory Action dated May 10, 2018.
U.S. Appl. No. 14/846,387, filed Sep. 4, 2015 Final Office Action dated Mar. 22, 2018.
U.S. Appl. No. 14/866,441, filed Sep. 25, 2015 Final Office Action dated Jun. 5, 2018.
U.S. Appl. No. 14/866,738, filed Sep. 25, 2015 Non-Final Office Action dated Nov. 6, 2017.
U.S. Appl. No. 15/154,808, filed May 13, 2016 Non-Final Office Action dated Apr. 6, 2018.
U.S. Appl. No. 15/154,808, filed May 13, 2016 Restriction Requirement dated Jan. 3, 2018.
U.S. Appl. No. 15/377,880, filed Dec. 13, 2016 Non-Final Office Action dated May 14, 2018.
U.S. Appl. No. 15/692,915, filed Aug. 31, 2017 Non-Final Office Action dated Jan. 29, 2018.
U.S. Appl. No. 29/536,043, filed Aug. 12, 2015 Final Office Action dated Mar. 26, 2018.
U.S. Appl. No. 29/545,436, filed Nov. 12, 2015 Final Office Action dated Mar. 26, 2018.
CN 201580022407.7 filed Nov. 2, 2016 Office Action dated Jan. 31, 2019.
EP 07783404.2 filed Jan. 19, 2009 Office Action dated Apr. 16, 2019.
JP 2018-039302 filed Mar. 6, 2018 Office Action dated Feb. 20, 2019.
U.S. Appl. No. 15/608,802, filed May 30, 2017 Non-Final Office Action dated Jun. 6, 2019.
U.S. Appl. No. 15/702,537, filed Sep. 12, 2017 Notice of Allowance dated Jul. 31, 2019.
U.S. Appl. No. 15/727,528, filed Oct. 6, 2017 Restriction Requirement dated Aug. 7, 2019.
CN 201580022407.7 filed Nov. 2, 2016 Office Action dated Sep. 16, 2019.
U.S. Appl. No. 15/727,528, filed Oct. 6, 2017 Non-Final Office Action dated Sep. 20, 2019.
U.S. Appl. No. 15/951,931, filed Apr. 12, 2018 Non-Final Office Action dated Nov. 19, 2019.
U.S. Appl. No. 15/951,954, filed Apr. 12, 2018 Non-Final Office Action dated Nov. 4, 2019.
U.S. Appl. No. 15/727,528, filed Oct. 6, 2017 Final Office Action dated Jan. 28, 2020.
U.S. Appl. No. 15/862,380, filed Jan. 4, 2018 Restriction Requirement dated Dec. 23, 2019.
U.S. Appl. No. 15/951,931, filed Apr. 12, 2018 Notice of Allowance dated Feb. 20, 2020.
U.S. Appl. No. 15/951,954, filed Apr. 12, 2018 Notice of Allowance dated Feb. 23, 2020.
U.S. Appl. No. 29/654,527, filed Jun. 25, 2018 Restriction Requirement dated Mar. 10, 2020.
EP 16797029.2 filed Nov. 21, 2017 Office Action dated Mar. 27, 2020.
EP17849786.3 filed Apr. 12, 2019 Extended European Search Report dated May 13, 2020.
U.S. Appl. No. 14/250,093, filed Apr. 10, 2014 Patent Board Decision dated Jun. 8, 2020.
U.S. Appl. No. 15/727,528, filed Oct. 6, 2017 Notice of Allowance dated Mar. 27, 2020.
U.S. Appl. No. 15/869,872, filed Jan. 12, 2018 Non-Final Office Action dated Apr. 10, 2020.
U.S. Appl. No. 15/951,931, filed Apr. 12, 2018 Notice of Allowability dated Apr. 16, 2020.
U.S. Appl. No. 15/951,954, filed Apr. 12, 2018 Notice of Allowability dated Apr. 7, 2020.
U.S. Appl. No. 16/138,523, filed Sep. 21, 2018 Notice of Allowance dated Mar. 26, 2020.
U.S. Appl. No. 29/654,521, filed Jun. 25, 2018 Restriction Requirement dated Apr. 8, 2020.
U.S. Appl. No. 29/658,136, filed Jul. 27, 2018 Restriction Requirement dated May 11, 2020.
U.S. Appl. No. 14/250,093, filed Apr. 10, 2014 Notice of Allowance dated Aug. 19, 2020.
U.S. Appl. No. 14/866,738, filed Sep. 25, 2015 Patent Board Decision dated Jul. 13, 2020.
U.S. Appl. No. 15/862,380, filed Jan. 4, 2018 Non-Final Office Action dated Jul. 9, 2020.
U.S. Appl. No. 15/869,872, filed Jan. 12, 2018 Final Office Action dated Jun. 25, 2020.
U.S. Appl. No. 16/292,076, filed Mar. 4, 2019 Non-Final Office Action dated Aug. 10, 2020.
U.S. Appl. No. 16/295,906, filed Mar. 7, 2019 Non-Final Office Action dated Sep. 4, 2020.
U.S. Appl. No. 29/654,521, filed Jun. 25, 2018 Notice of Allowance dated Aug. 17, 2020.
U.S. Appl. No. 29/654,527, filed Jun. 25, 2018 Notice of Allowance dated Aug. 18, 2020.
U.S. Appl. No. 29/658,136, filed Jul. 27, 2018 Non-Final Office Action dated Sep. 9, 2020.
EP 19181963.0 filed Jun. 24, 2019 Extended European Search Report dated Jul. 16, 2019.
PCT/US2019/021231 filed Mar. 7, 2019 International Search Report and Written Opinion, dated Jun. 27, 2019.
U.S. Appl. No. 14/866,738, filed Sep. 25, 2015 Notice of Allowance dated Sep. 24, 2020.
U.S. Appl. No. 15/862,380, filed Jan. 4, 2018 Final Office Action dated Oct. 26, 2020.
U.S. Appl. No. 15/869,872, filed Jan. 12, 2018 Advisory Action dated Sep. 23, 2020.
U.S. Appl. No. 29/654,521, filed Jun. 25, 2018 Notice of Allowability dated Sep. 30, 2020.
U.S. Appl. No. 29/654,527, filed Jun. 25, 2018 Notice of Allowability dated Sep. 30, 2020.
U.S. Appl. No. 16/292,076, filed Mar. 4, 2019 Corrected Notice of Allowance dated Feb. 25, 2021.
U.S. Appl. No. 16/292,076, filed Mar. 4, 2019 Notice of Allowance dated Feb. 4, 2021.
U.S. Appl. No. 16/295,906, filed Mar. 7, 2019 Final Office Action dated Dec. 22, 2020.
U.S. Appl. No. 16/295,906, filed Mar. 7, 2019 Notice of Allowance dated Mar. 4, 2021.
U.S. Appl. No. 16/296,087, filed Mar. 7, 2019 Restriction Requirement dated Feb. 8, 2021.

(56) References Cited

OTHER PUBLICATIONS

U.S. Appl. No. 16/529,602, filed Aug. 1, 2019 Notice of Allowance dated Jan. 19, 2021.

* cited by examiner

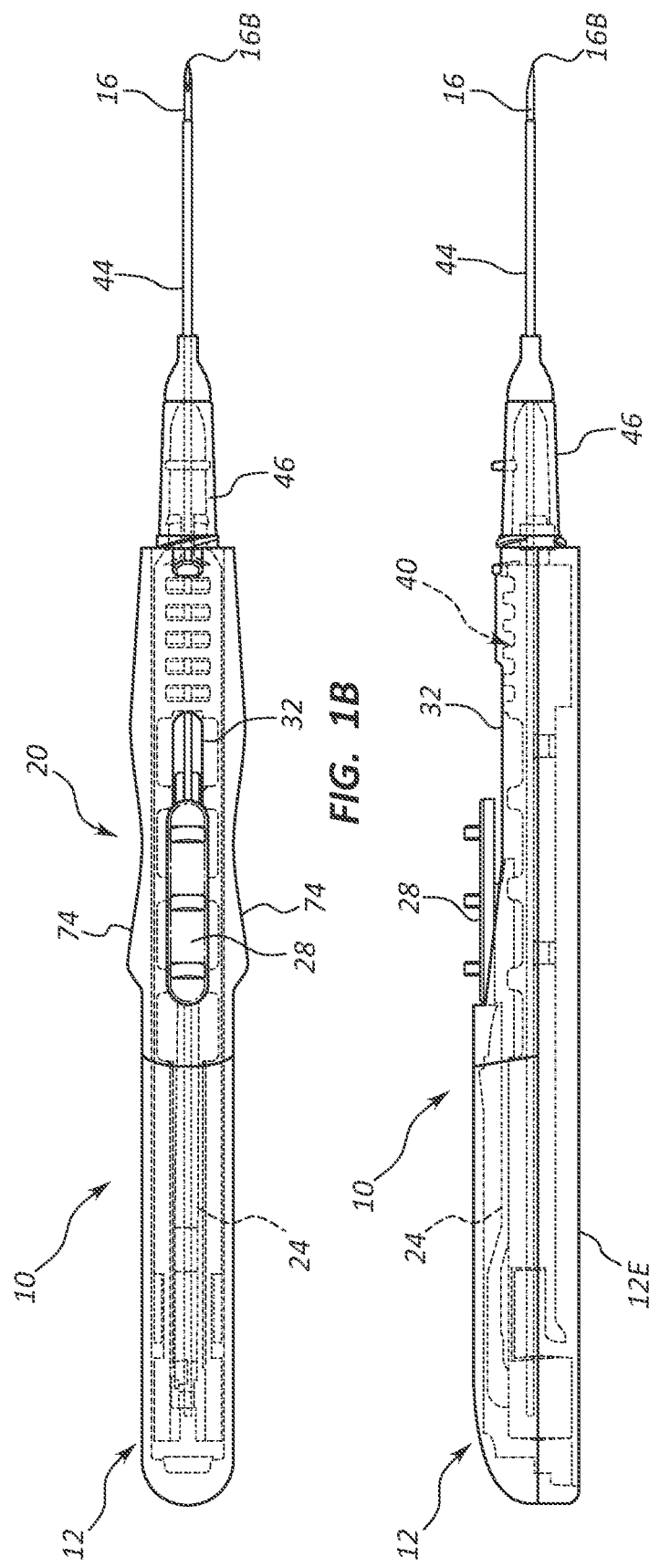
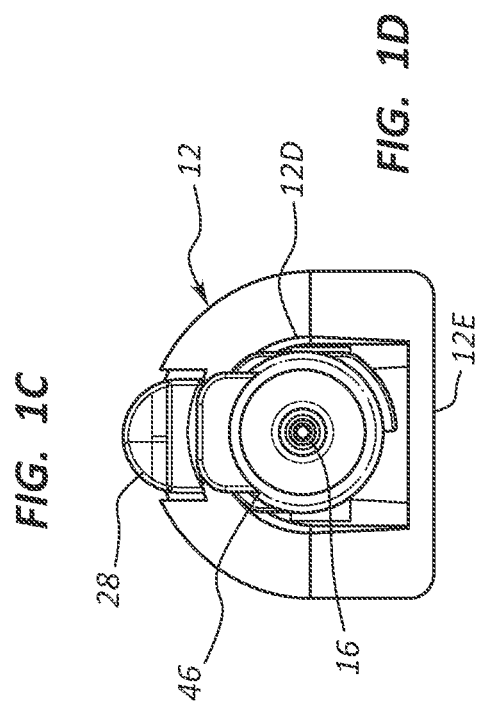

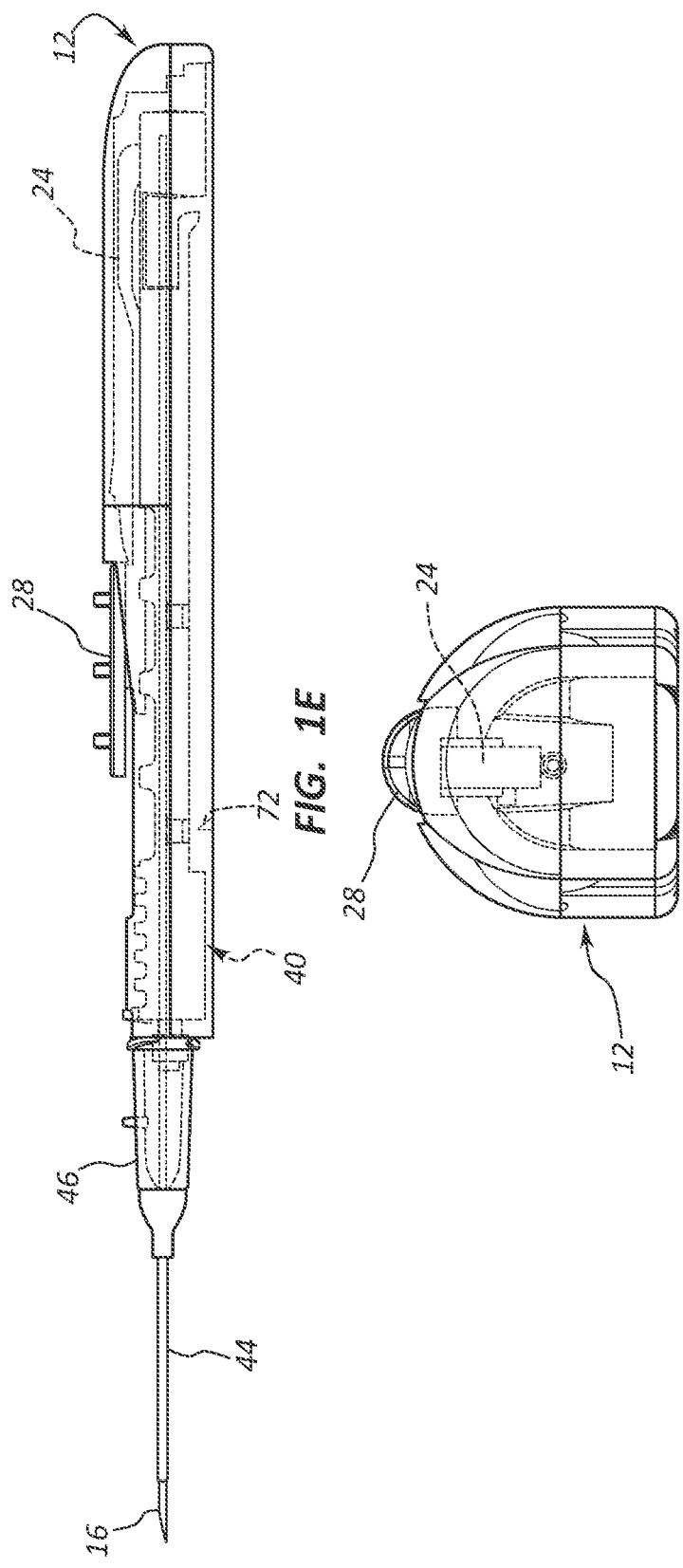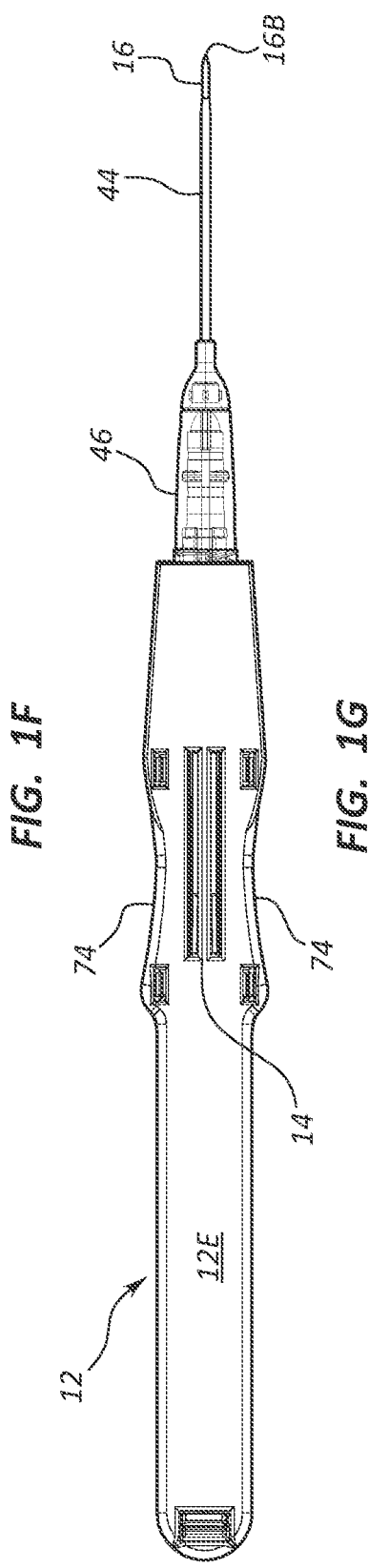

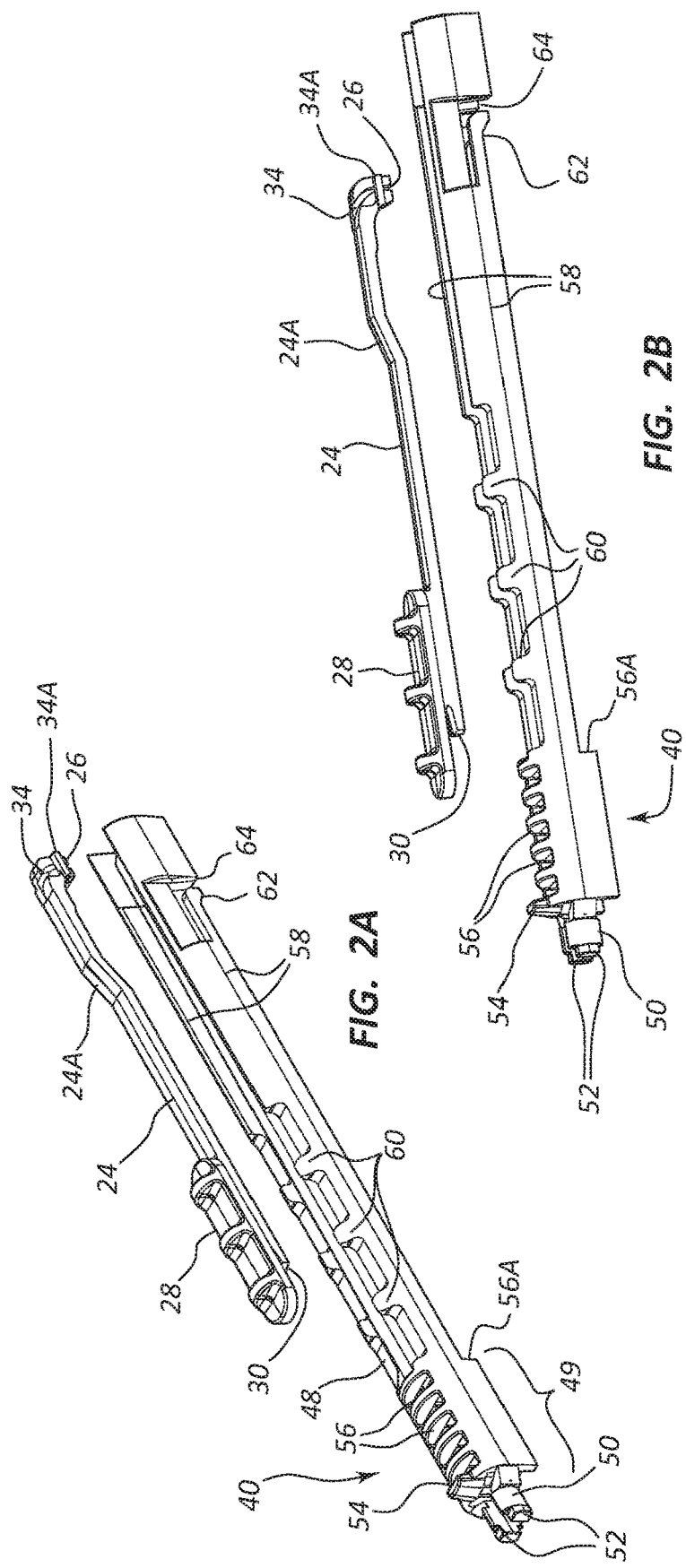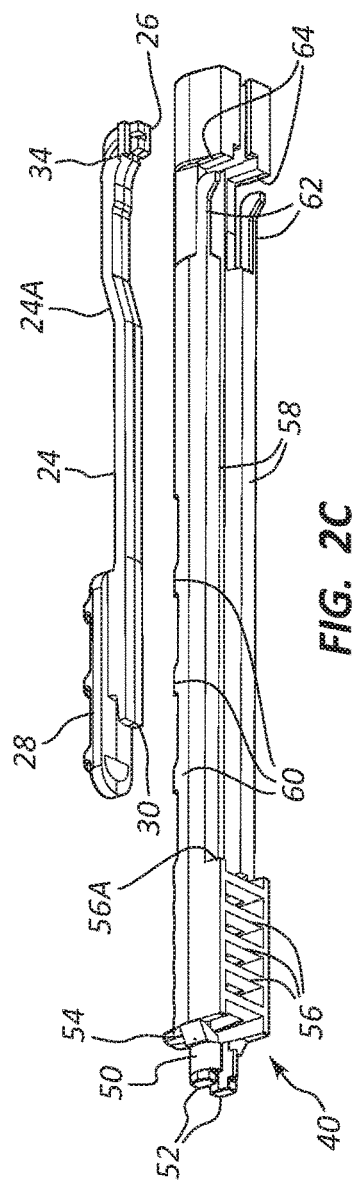

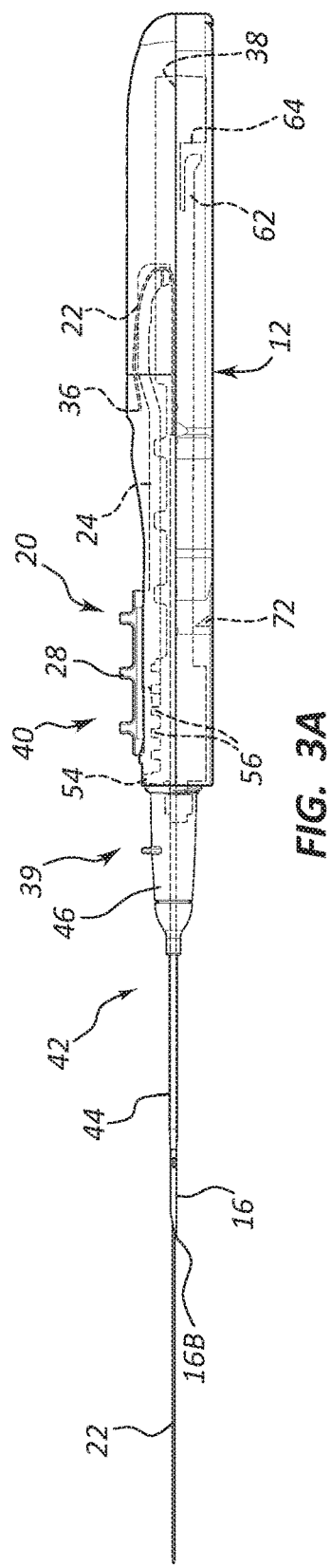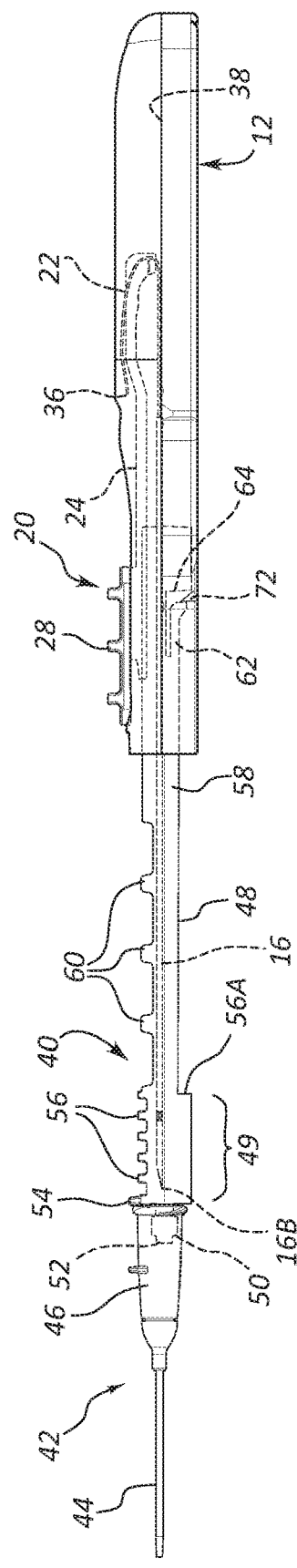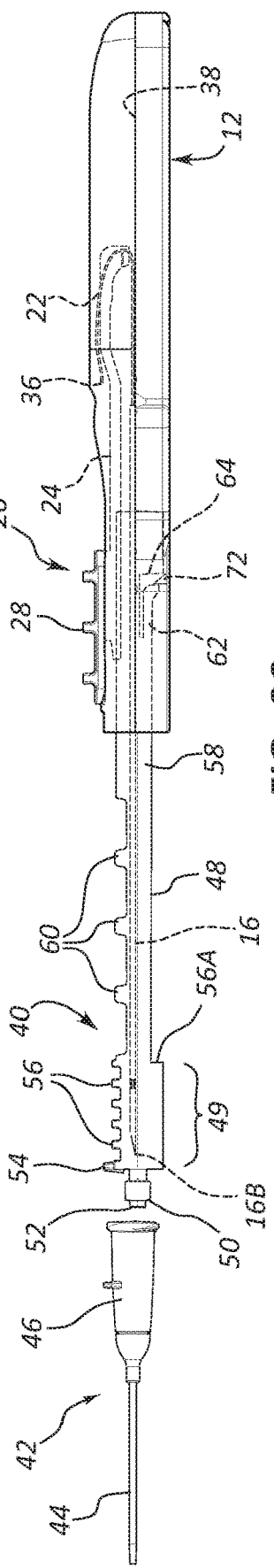

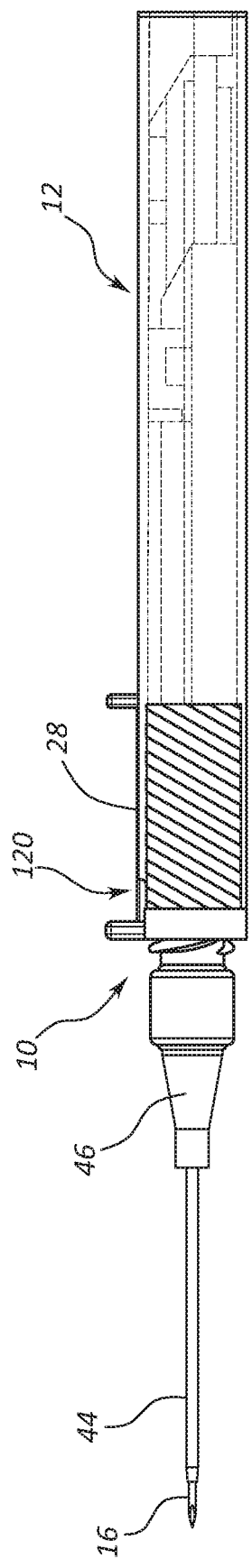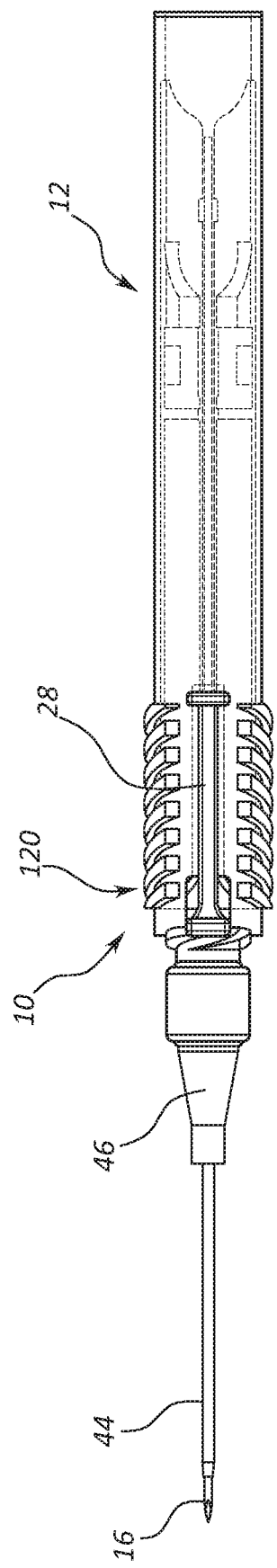
FIG. 8B
FIG. 8C

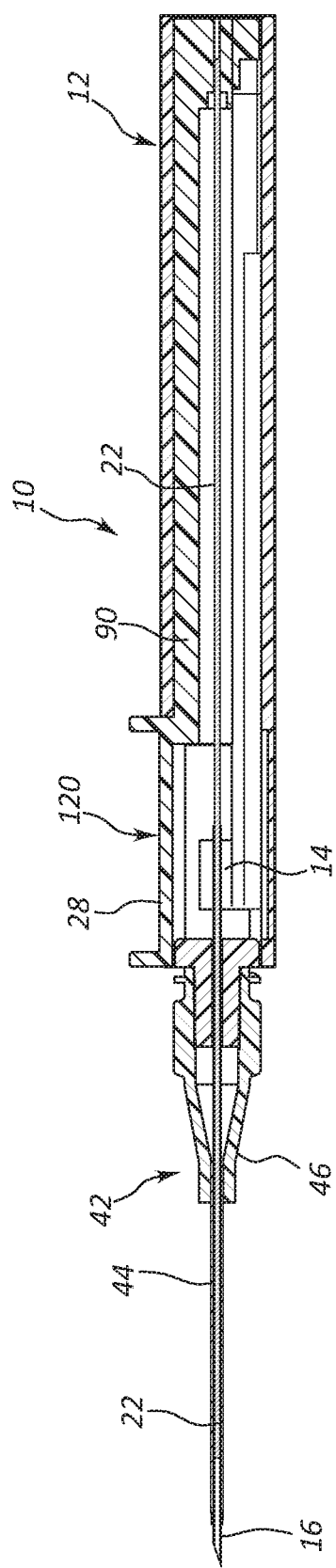
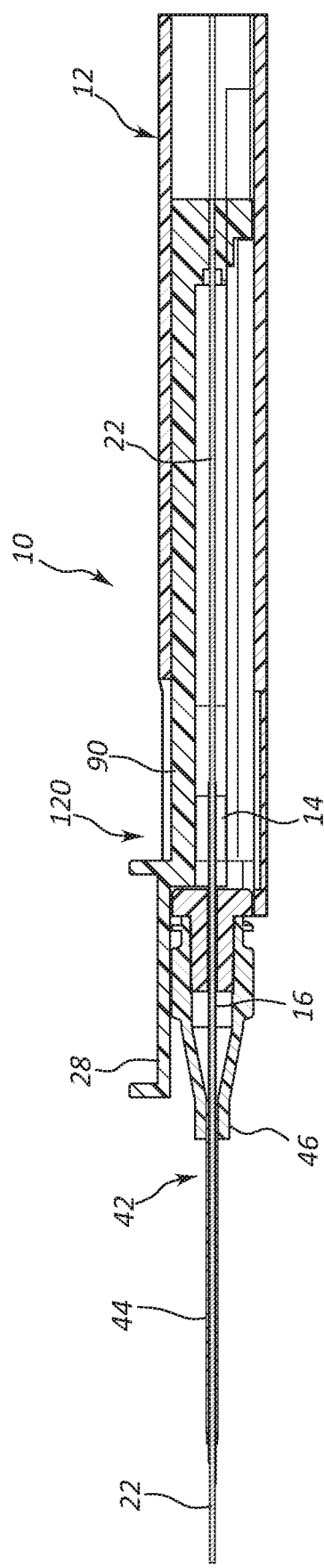
FIG. 8E
FIG. 8F

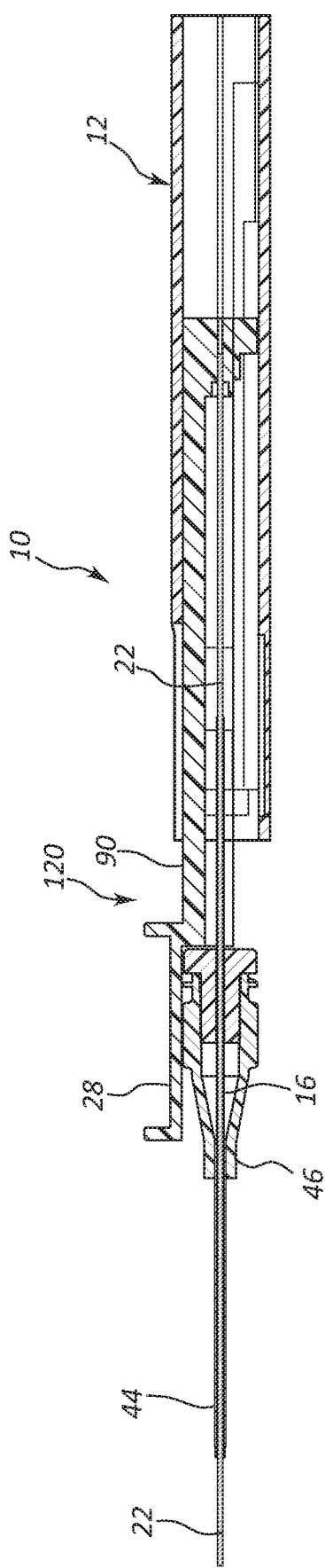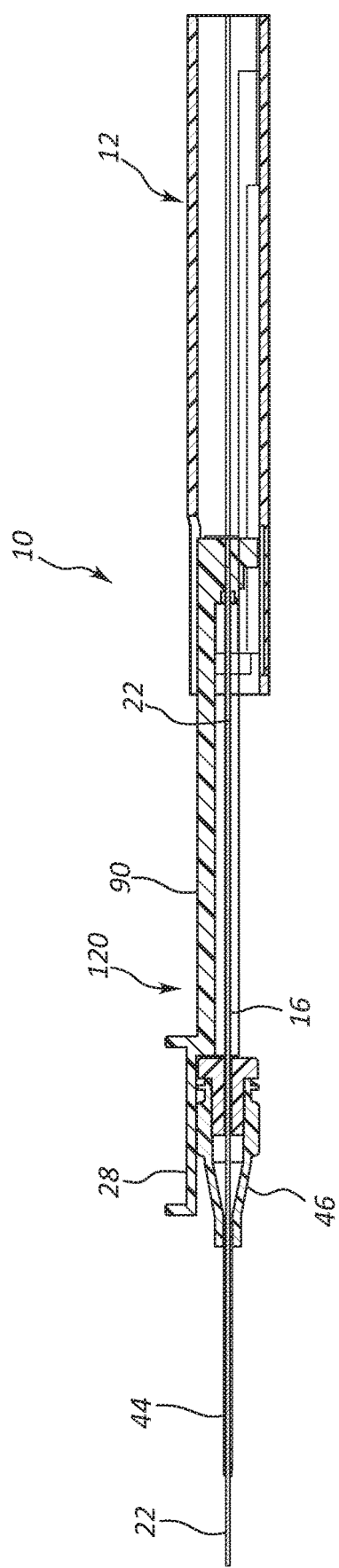

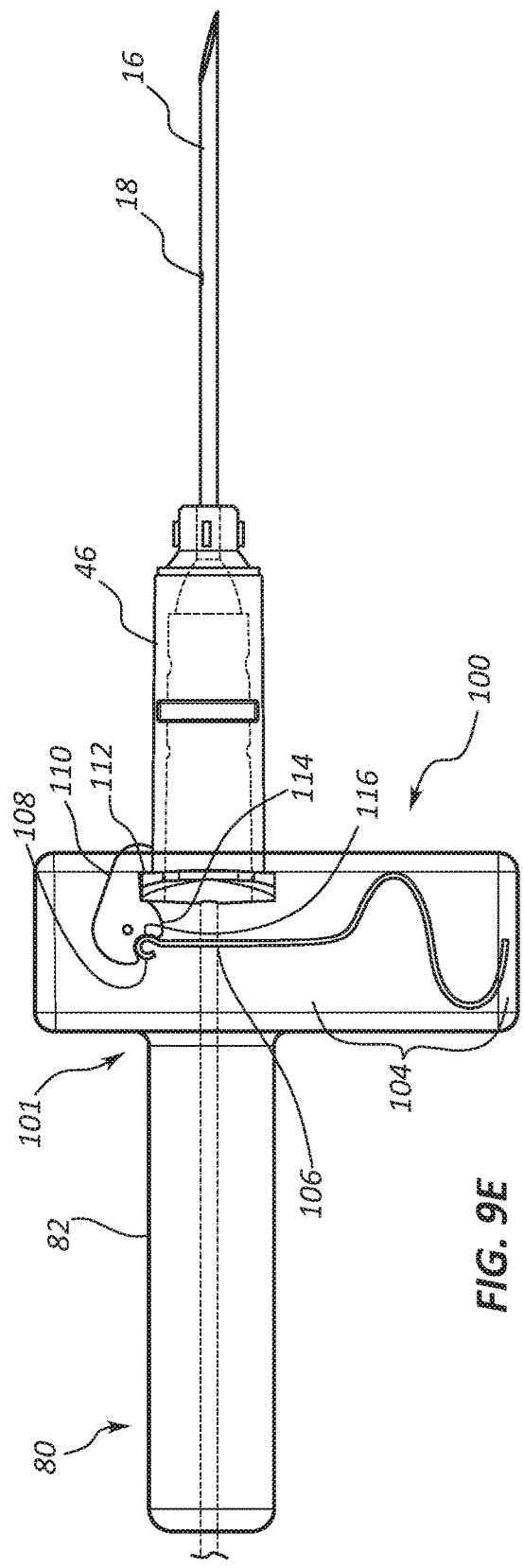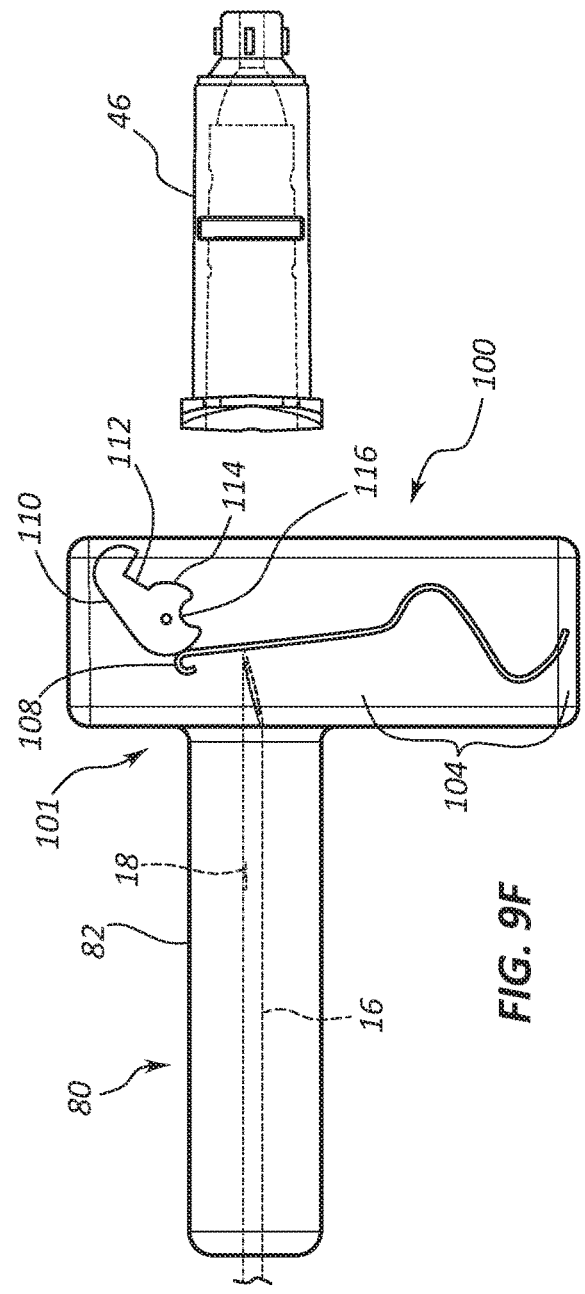
FIG. 9E
FIG. 9F

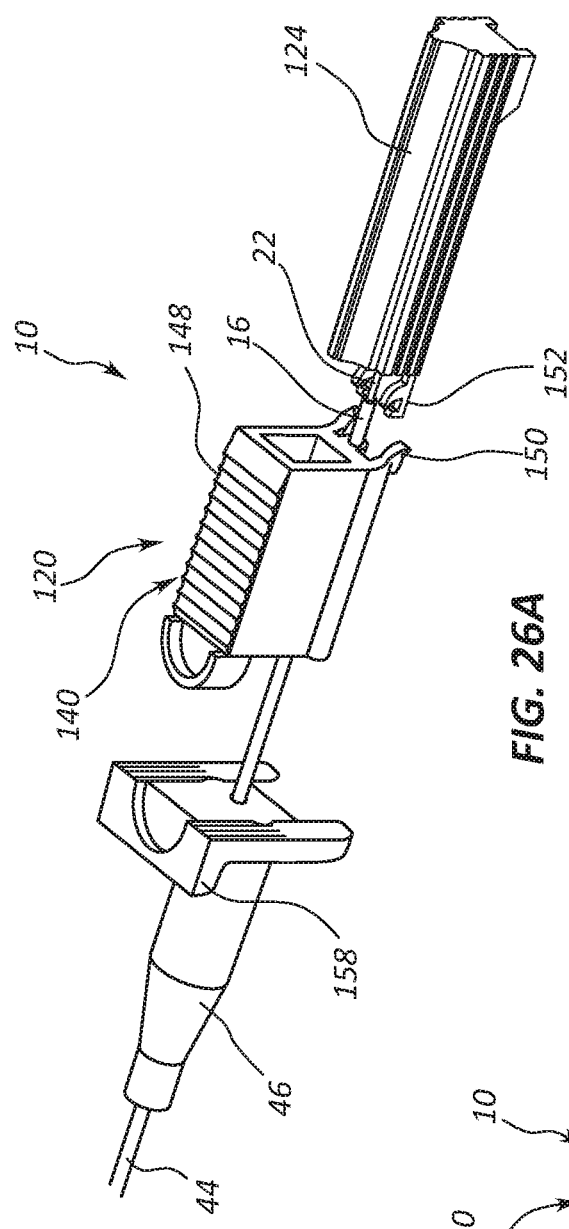
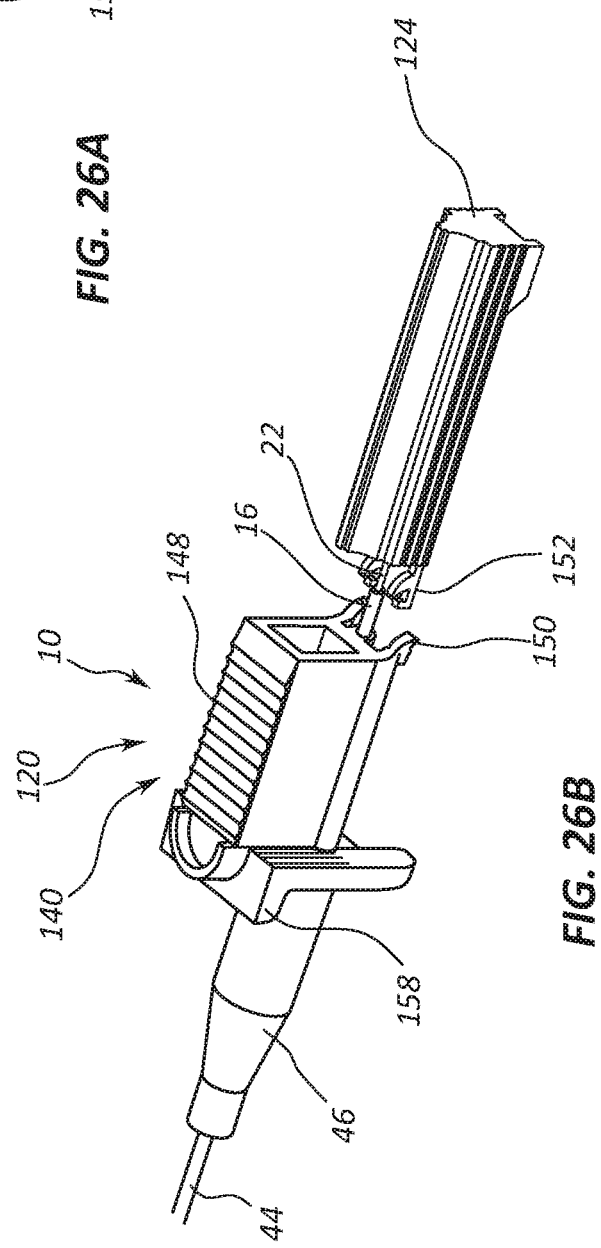
FIG. 26A
FIG. 26B

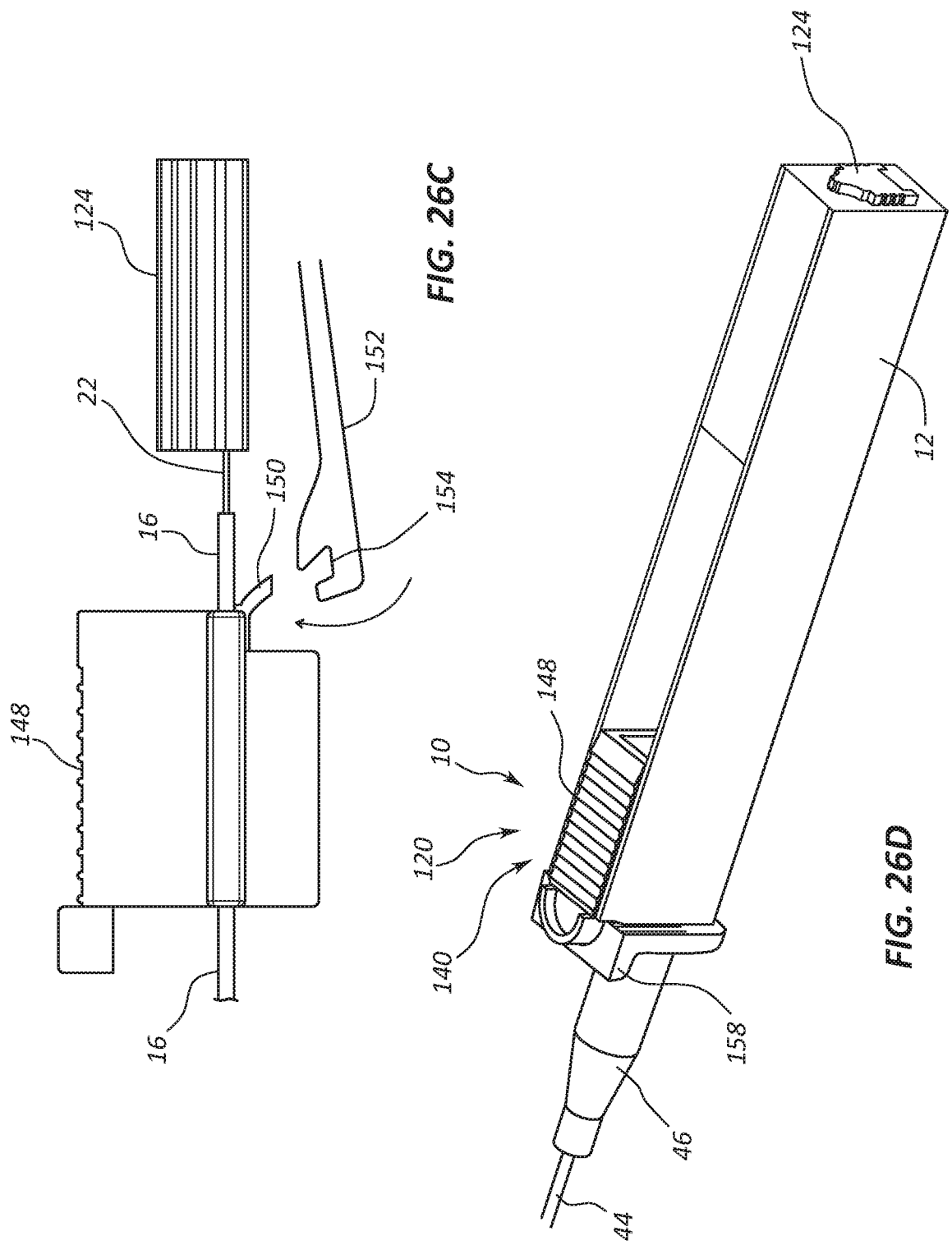

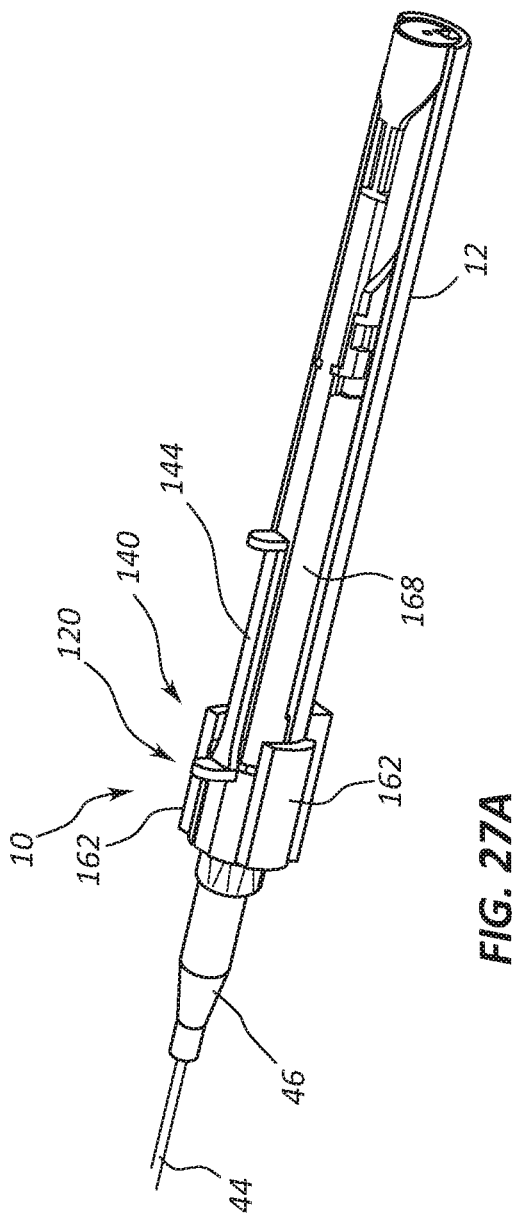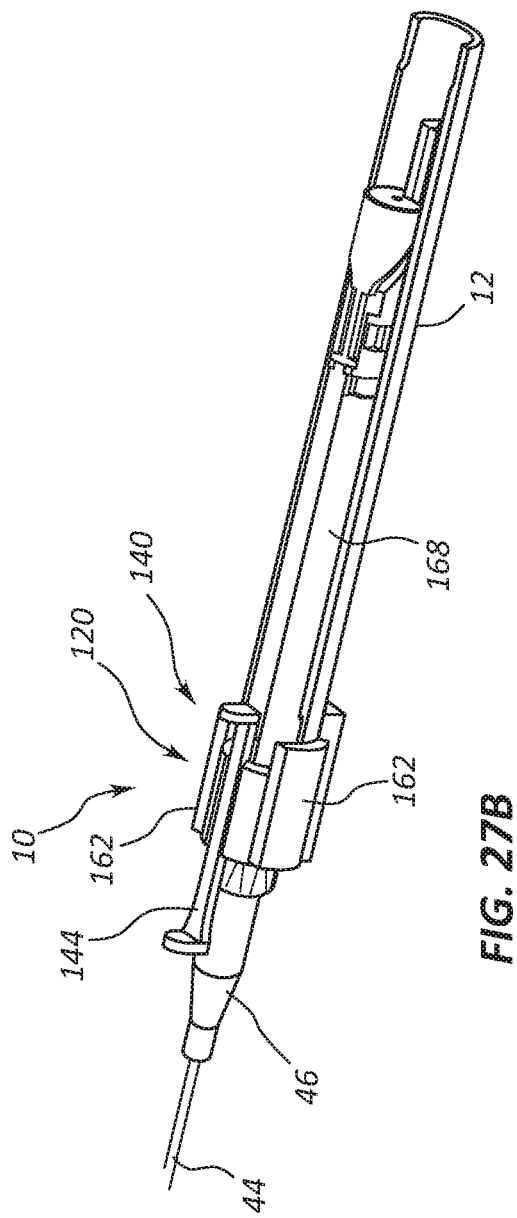
FIG. 27A
FIG. 27B

CATHETER PLACEMENT DEVICE INCLUDING AN EXTENSIBLE NEEDLE SAFETY COMPONENT

CROSS-REFERENCE TO RELATED APPLICATIONS

This application claims the benefit of U.S. Provisional Patent Application No. 62/162,548, filed May 15, 2015, and titled "Catheter Placement Device Including an End-Mounted Advancement Component," which is incorporated herein by reference in its entirety.

BRIEF SUMMARY

Briefly summarized, embodiments of the present invention are directed to an insertion device for inserting a catheter or other tubular medical device into a body of a patient. The insertion device combines needle insertion, guidewire advancement, catheter insertion, and needle shielding in a single device. In one embodiment, the insertion device comprises a housing and a hollow needle that distally extends from the housing. At least a portion of the catheter is pre-disposed over the needle such that the catheter is disposed substantially external to the housing. A guidewire is included, as well as an advancement assembly that is configured to selectively advance the distal end of the guidewire out a distal opening of the needle in preparation for distal advancement of the catheter. The advancement assembly is further configured to enable selective advancement of the catheter in a distal direction. The insertion device is configured to be grasped and used by a single hand of a user during advancement of the guidewire and the catheter.

In another embodiment, continuous blood flash indicators are disclosed to assist in confirming that the needle of the catheter insertion device has accessed and remains in a vein or other blood-carrying vessel. In yet another embodiment, needle safety components are disclosed for use with the catheter insertion device.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 1A-1J show various views of a catheter insertion tool according to one embodiment;

FIGS. 2A-2C show various views of components of the catheter insertion tool of FIGS. 1A-1J;

FIGS. 3A-3C show various stages of use of the catheter insertion tool of FIGS. 1A-1J;

FIGS. 8A-8H are various views of a catheter insertion tool according to one embodiment;

FIGS. 9A-9G are various views of a needle safety component according to one embodiment;

FIGS. 26A-26D are various views of a catheter insertion tool according to one embodiment;

FIGS. 27A-27E are various views of a catheter insertion tool according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a tool for assisting with the placement into a patient of a catheter or other tubular medical device. For example, catheters of various lengths are typically placed into a body of a patient so as to establish access to the patient's vasculature and enable the infusion of medicaments or aspiration of body fluids. The catheter insertion tool to be described herein facilitates such catheter placement. Note that, while the discussion below focuses on the placement of catheters of a particular type and relatively short length, catheters of a variety of types, sizes, and lengths can be inserted via the present device, including peripheral IVs, intermediate or extended-dwell catheters, PICCs, central venous catheters, etc. In one embodiment, catheters having a length between about 1 inch and about 1.9 inches can be placed, though many other lengths are also possible.

Figure 1A:
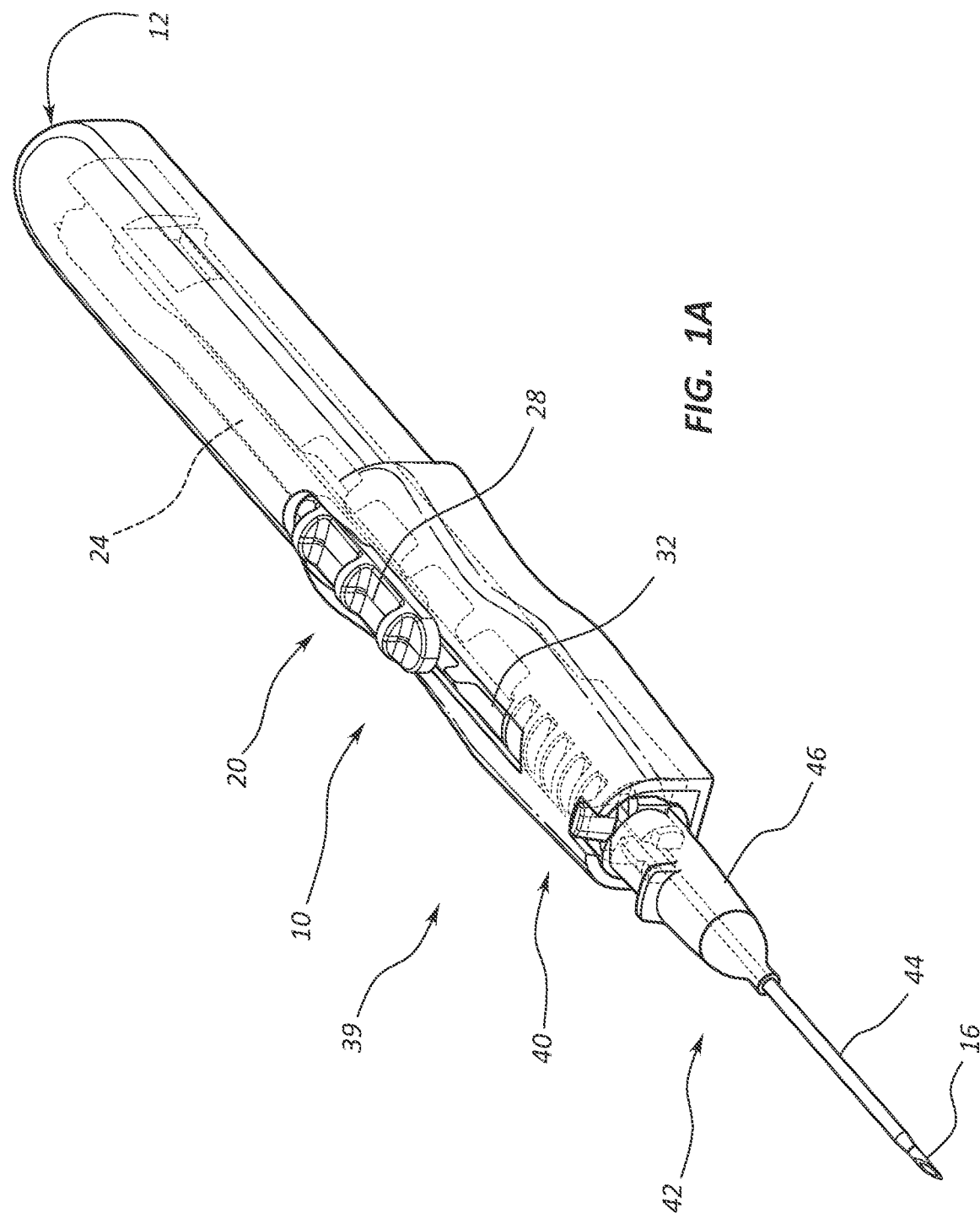

FIGS. 1A-1J depict various details regarding a catheter insertion tool ("insertion tool" or "insertion device"), generally depicted at 10, according to one embodiment. As shown, the insertion tool 10 includes a housing 12 that may itself include a top front housing portion 12A, a top back housing portion 12B, and a bottom housing portion 12C mated with one another via tabs and slots 78 or other suitable attachment modes. The housing 12 further includes an open distal end 12D, and a flat bottom 12E to enable the insertion device 10 to lie flat on a surface without tipping. In another embodiment, the housing is integrally formed. In yet another embodiment, only a top housing portion and a bottom housing portion are employed. In the present embodiment, the housing composed of a thermoplastic such as polycarbonate and is translucent, though other configurations are contemplated. A rib 38 runs along the longitudinal length of the bottom housing portion 12C, in the present embodiment. The housing 12 defines grip surfaces 74 on either side of the housing, as seen in FIGS. 1B and 1G, to enable grasping of the insertion device 10 by the user.

A needle hub 14 supporting a hollow needle 16 (which together form part of a needle assembly, in one embodiment) is included with the housing 12. In the present embodiment, the needle hub 14 is integrally formed with the housing 12 within a cavity 70 defined by the housing, as best seen in FIG. 1I, though the needle hub can be configured in other ways. The needle hub 14 includes a pocket 14A for receiving a portion of the needle 16 and a quantity of adhesive, such as liquid or UV-cure adhesive for example, in order to fix the needle in place in the needle hub. The needle 16 extends distally from the needle hub 14 so as to extend out an open distal end 12D of the housing 12 and terminates at a distal end 16B. A notch 18 is defined through the wall of the needle 16 proximate the distal end thereof. The notch 18 enables flashback of blood to exit the lumen defined by the hollow needle 16 once access to the patient's vasculature is achieved during catheter insertion procedures. Thus, blood exiting the notch 18 can be viewed by a clinician to confirm proper needle placement in the vasculature, as will be explained further below.

A catheter 42 is removably disposed on the portion of the needle 16 residing external to the housing 12 such that the needle occupies a lumen of the catheter defined by a catheter tube 44. The catheter tube 44 extends distally from a hub 46 of the catheter 42, which hub is initially disposed adjacent the open distal end 12D of the housing 12, as shown in FIG. 1A-1C.

The insertion tool 10 further includes a guidewire advancement assembly 20 for advancing a guidewire 22 through the needle 16 and into the vasculature of the patient once access by the needle has been achieved. The guidewire 22 (FIG. 1I) is pre-disposed within the lumen of the needle 16. The guidewire advancement assembly 20 includes a guidewire lever 24 that selectively advances the guidewire 22 in a distal direction during use of the insertion tool 10 such that the distal portion of the guidewire extends beyond the distal end 16B of the needle 16. A finger pad 28 of the guidewire lever 24 is slidably disposed on the housing 12 via a slot 32 to enable a thumb and/or finger(s) of the user to selectively advance the guidewire 22 distally past the distal end 16B of the needle 16. Of course, other engagement schemes to translate user input to guidewire movement could also be employed. In the present embodiment, the guidewire 22 includes a guidewire support tube 19 (FIGS. 1I, 1J) to provide additional stiffness to the guidewire and facilitate its distal advancement described above.

Figure 1H:
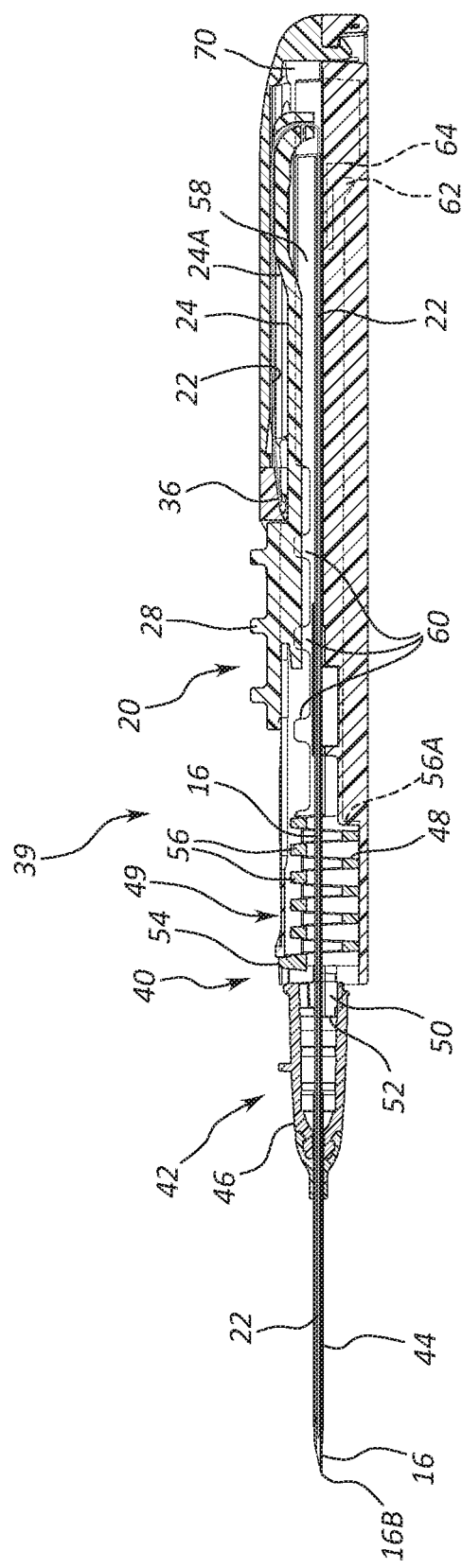
Figure 1I:
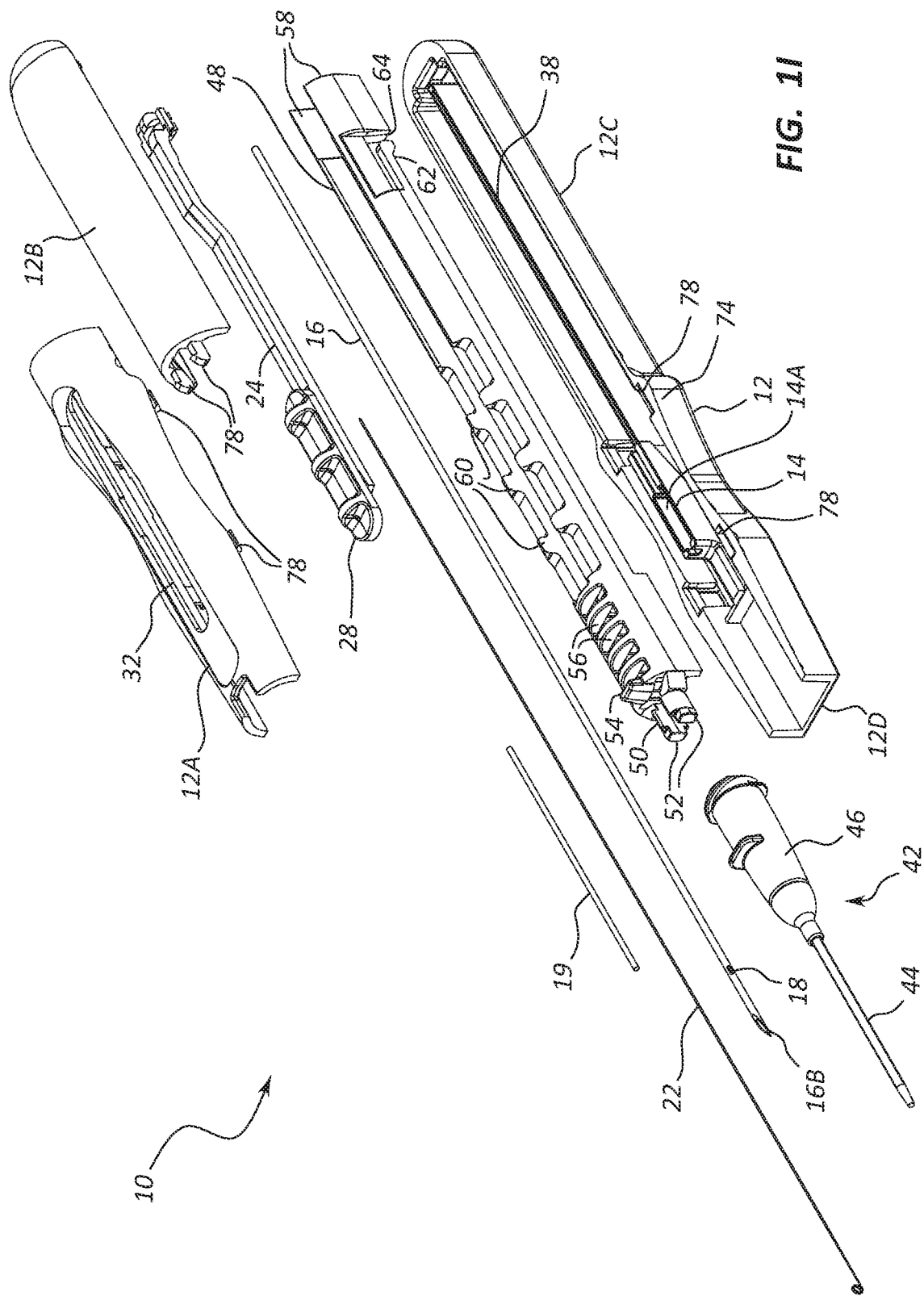

Together with FIG. 1H, reference is made to FIGS. 2A-2C in describing further details of the insertion tool 10 of FIGS. 1A-1J. Further details of the guidewire lever 24 are shown, including a lever tab 26 at the proximal end of the guidewire lever that is used as described below in distally advancing the guidewire 22. An angled portion 24A of the guidewire lever 24 is disposed distal to the lever tab 26. A push tab 30 is defined below the finger pad 28 and is employed during distal advancement of the guidewire lever 24 to partially advance the catheter 42 distally, as will be described below.

In the present embodiment, a proximal end of the guidewire 22 is attached at an anchor point 36 on an interior portion of the housing 12 (or other fixed portion of the insertion tool 10) and looped about the proximal portion of the guidewire lever 24 in a roughly U-shaped configuration (FIG. 1H) such that the distal end of the guidewire extends two units of distance distally past the distal end 16B of the needle 16 for every one unit of distance of movement of the finger pad 28.

In greater detail, FIGS. 2A-2C show that curved guide surfaces 34 are defined on the proximal end of the guidewire lever 24 to enable an intermediate portion of the guidewire 22 to loop back on itself proximate the proximal end of the device 10. The guide surfaces 34 constrain the flexible guidewire 22 into the looped, substantially U-shaped configuration. The angled portion 24A of the guidewire lever 24 helps to maintain the radius of the U-shaped portion of the guidewire 22 large enough so as to prevent kinking/undesired bending of the guidewire as it loops back. The looped-back intermediate portion of the guidewire 22 then extends toward the distal end of the device 10 within the cavity 70 of the housing 12 before it enters the lumen of the needle 16 at a proximal end of the needle, which is secured by the needle hub 14. A bar 34A is positioned across the guide surfaces 34 in the present embodiment to keep the guidewire 22 in contact with the guide surfaces. In one embodiment, the rib 38 can include a channel in which a portion of the intermediate portion of the looped guidewire 22 can reside so as to guide the guidewire toward the proximal end of the needle 16.

So configured, the free distal end of the guidewire 22 initially resides within the lumen of the needle 16 and is positioned for selective advancement by the guidewire advancement assembly 20 such that the free distal end thereof can distally extend from the open distal tip of the needle 16. This selective advancement of the guidewire 22 is achieved in the present embodiment via distal movement of the finger pad 28 included on the device housing 12.

Distal movement of the finger pad 28 causes corresponding distal sliding movement of the guidewire lever 24. The guide surfaces 34 of the guidewire lever 26 push the bend of the guidewire 22 distally as the guidewire lever 24 advances. Note that the guidewire 22 is sufficiently rigid, in part due to the guidewire support tube 19, so as to be advanced by the guidewire lever 24 without buckling. Also, the guide surfaces 34 and guidewire 22 are configured to enable retraction of the guidewire 22 back into the insertion device housing 12 when the finger pad 28 (or other suitable mechanism in other embodiments) is slid proximally.

This distal sliding movement of the guidewire lever 24 causes the distal end of the guidewire 22 to extend distally from the open distal tip 16B of the needle 16. Because of its anchored proximal end at the anchor point 36 and its bent or looped U-shape configuration (FIG. 1H), the guidewire 22 is distally advanced at a linear rate of about twice the linear advancement rate of finger pad 28, which results in about twice the length of guidewire extension when compared with the length of movement of the guidewire advancement slide 28. This further desirably results in a relatively longer length of guidewire extension into the vein or other patient vessel so as to more suitably guide the catheter 42 into the patient's body. As such, the guidewire advancement assembly described here operates as a type of "reverse pulley" system for distal guidewire advancement. Note that other looping configurations of the guidewire can be included with the device 10 in addition to those shown and described herein. Also, differing ratios of guidewire extension vs. advancement assembly movement are also possible in other embodiments.

Note that the above-described structures for providing a looping guidewire are only examples of structures that can suitably perform the desired functionality described herein. Indeed, other structures can be employed to accomplish the principles described in connection with the present embodiment. Also, though shown and described above to be attached to the catheter insertion device housing, the proximal end of the guidewire can be attached to other structures within/on the device, such as the needle hub 14, for instance. The majority length of the guidewire in one embodiment includes a metal alloy of nickel and titanium commonly referred to as nitinol, which is sufficiently rigid and can be disposed in the U-shaped configuration without retaining a memory of that position when the guidewire is advanced. Note that other suitable guidewire materials can also be employed.

The insertion tool 10 further includes a catheter advancement assembly 40 for selectively advancing in a distal direction the catheter 42, pre-disposed on the needle 16 external to the housing 12. In particular, the catheter advancement assembly 40 includes an advancement member 48 that initially resides within the cavity 70 defined by the housing 12 and is used in selectively advancing the catheter 42 in a distal direction during use of the insertion tool 10 to insert the catheter into the body of the patient. As will be seen, the advancement member 48 also acts as a needle safety component for shielding the needle 16 from the user after use of the device 10 is complete, as will be described further below.

FIGS. 2A-2C depict further details of the advancement member 48 of the catheter advancement assembly 40 according to the present embodiment. As shown, the advancement member 48 defines an elongate body that is configured to straddle the needle 16 when the advancement member 48 is initially disposed within the housing cavity 70. The body of the advancement member 48 includes a distal portion 49. A pair of hub engagement tabs 50 extend distally from the distal end of the distal portion 49, and each engagement tab includes a radially extending protuberance 52. When the advancement member 48 is disposed within the housing 12, the needle 16 passes distally between the engagement tabs 50, as seen in FIG. 1H. The advancement member 48 is configured such that the needle 16 extends the engagement tabs 50 a relatively small distance radially outward while the needle is disposed therebetween. The catheter 42, when disposed over the needle 16, as seen in FIG. 1H, is kept in place against the open housing distal end 12D via the protuberances 52 of the engagement tabs 50 producing a friction fit against an inner surface of the catheter hub 46. As will be seen further below, when the needle 16 is no longer disposed between the engagement tabs 50, the tabs withdraw radially inward, allowing the catheter to separate from the distal end of the advancement member 48.

The distal portion 49 of the advancement member 48 further includes an advancement tab 54 for assisting with manual distal extension of the advancement tab during deployment of the catheter 42, and a plurality of top and bottom ribs 56 that extend across the advancement member body to join two elongate arms 58 that longitudinally extend proximally from the distal portion. FIGS. 1G and 1H show that the arms 58 straddle the needle 16 when the advancement member 48 is initially disposed in the cavity 70 of the housing 12. The top and bottom ribs 56 are positioned such that the distal tip 16B of the needle 16 is shielded from user contact after extension of the advancement member 48 from the housing 12 is complete, as discussed further below. In addition, a proximal end 56A of the ribs 56 (FIG. 1H) acts as a stop against a pair of lock wedges 72, formed in the housing 12, to prevent further proximal entry of the advancement member 48 into the housing cavity 70.

Each of the arms 58 includes secondary tabs 60 disposed proximal to the distal portion 49 to assist, together with the advancement tab 54, in manually extending the advancement member 48 in the distal direction by enabling locations for a finger of the user to push against. Proximate the proximal end of each advancement member arm 58, a locking tab 62 is included. The locking tabs 62 are deformable to enable them to pass over the lock wedges 72 when the advancement member 48 is distally extended during catheter distal advancement (described below) so as to prevent re-entry of the advancement member into the housing cavity 70, which also ensures that the distal tip 16B of the needle 16 remains shielded by the ribs 56 of the advancement member distal portion 49. In addition, stop surfaces 64 are included on the advancement member arms 58 proximal to each locking tab 62 so as to prevent the advancement member 48 from completely separating from the housing 12 when the advancement member is distally extended from the housing. This is accomplished by each stop surface 64 engaging with a respective one of the lock wedges 72, which prevents further distal movement of the advancement member. Thus, after full distal extension, the advancement member 48 is locked from either proximal movement to cause re-entry of the advancement member into the housing cavity 70 via engagement of the locking tabs 62 with the lock wedges 72, or further distal movement via engagement of the stop surfaces 64 with the lock wedges. In addition to these, other modes for preventing undesired proximal and distal movement of the advancement member after distal extension thereof can also be employed.

Note that in one embodiment the outer diameters of the needle 16 and the catheter tube 44 are lubricated with silicone or other suitable lubricant to enhance sliding of the catheter tube with respect to the needle and for aiding in the insertion of the catheter into the body of the patient.

FIGS. 3A-3C depict various stages of use of the insertion device 10 in placing the catheter 42 in the vasculature of a patient. For clarity, the various stages are depicted without actual insertion into a patient being shown. With the insertion tool 10 in the configuration shown in FIG. 1E, a user grasping the insertion device 10 first guides the distal portion of the needle 16 through the skin at a suitable insertion site and accesses a subcutaneous vessel.

After needle access to the vessel is confirmed, the guidewire advancement assembly 20 is actuated, wherein the finger pad 28 (disposed in the slot 32 defined in the housing) is advanced by the finger of the user to distally advance the guidewire 22 (FIG. 3A), initially disposed within the hollow needle 16. Note that the guidewire 22 is distally advanced by the guidewire lever 24, which is operably attached to the slidable finger pad 28.

Distal advancement of the guidewire 22 continues until the finger pad 28 has been distally slid a predetermined distance, resulting in a predetermined length of the guidewire 22 extending past the distal end of the needle 16, as shown in FIG. 3A.

At this point, the finger pad 28 is slid distally an additional distance, which causes the push tab 30 (FIG. 2B) of the guidewire lever 24 to abut against the proximal end 56A of the ribs 56 of the advancement member 48 of the catheter advancement assembly 40. This in turn causes the advancement member 48 to distally advance out the open distal end of the housing 12D a predetermined distance. As it is removably attached to the distal portion 49 of the advancement member 48 via the hub engagement tabs 50, the catheter 42 is also distally advanced the predetermined distance. Distal advancement of the advancement member 48 ceases when the notch above the guidewire lever push tab 30 contacts the distal end of the slot 32 (FIG. 1I) defined in the housing 12 and stops further distal sliding of the finger pad 28.

Once the guidewire lever 24 has been fully distally extended via sliding of the finger pad 28, which in turn has extended the guidewire 22 past the distal end 16B of the needle 16 and into the vessel of the patient and has distally advanced the advancement member 48 and connected catheter 42 a predetermined distance away from the device housing 12, further manual distal advancement of the advancement member 48 is performed by a finger of the user via pushing against the advancement tab 54 and then the secondary tabs 60 of the advancement member, as seen in FIG. 3B. This causes the catheter tube 44 to slide over distal portions of the needle 16 and guidewire 22 and into the patient's vasculature via the insertion site. In light of this, it is appreciated that the finger pad 28 acts as a first member used to advance the guidewire 22, whereas the advancement tab 54 acts as a second member used to advance the catheter 42, in the present embodiment. It is appreciated that the finger pad 28 is distally slidable to a distal termination point that is proximate a proximal commencement point of the second member such that movement of a finger of the user from the finger pad 28 to the advancement tab 54 occurs without substantial repositioning of the finger, in the present embodiment.

The advancement member 48 and connected catheter 42 are manually distally advanced until the advancement member has been fully extended, as seen in FIG. 3B, i.e., the locking tabs 62 slide over and lock with the lock wedges 72 defined by the housing 12, thus locking the advancement member from further distal advancement. In this fully extended state of the advancement member 48, the distal portion 49 is disposed over the needle 16 and shielded by the ribs 56. Thus, the advancement member 48 serves as one example of a needle safety component, according to the present embodiment. The engagement of the above-mentioned locking tabs 62, as well as the stop surfaces 64, of the advancement member 48 with the lock wedges 72 prevents further distal or proximal movement of the advancement member, thus desirably ensuring continued shielding of the distal end 16B of the needle 16.

The above distal advancement of the advancement member 48 likewise distally advances the catheter tube 44 over the needle 16 and guidewire 22 and into the vessel of the patient until the catheter hub 46 abuts the insertion site of the needle through the skin. As the needle 16 is no longer disposed between them, the hub engagement tabs 50 compress radially inward, thus releasing the friction fit between the protuberances 52 and the interior surface of the catheter hub. This enables the catheter 42 to be separated from the advancement member 48, as shown in FIG. 3C. The catheter 42, now in place in the patient, can be prepared for use and dressed down, per standard procedures. Then insertion device 10 can be discarded.

In light of the above, it is appreciated that the guidewire advancement assembly 20 and the catheter advancement assembly 40 operate in conjunction with one another in the present embodiment and thus comprise together a master advancement assembly for placing the catheter 42. It is further appreciated that the master advancement assembly can include both or only one of a guidewire advancement assembly and a catheter advancement assembly in other embodiments.

It is noted that the device 10 is configured such that grasping of the device and advancement of the guidewire 22 and the catheter 42 can be performed by only one hand of the user. This is accomplished in the present embodiment by placing the grip surfaces 74 and the finger pad 28 in convenient locations for user grasping of the device 10, together with enabling the finger pad 28 and guidewire advancement assembly 20 to be used to advance the guidewire 22 and the catheter 42 a predetermined distance, followed by manual advancement of the advancement member 48 by a finger of the user. This can be performed by a single thumb, finger, or fingers of the user, in the present embodiment. Of course, other grasping and advancement configurations can be employed.

Figure 4:
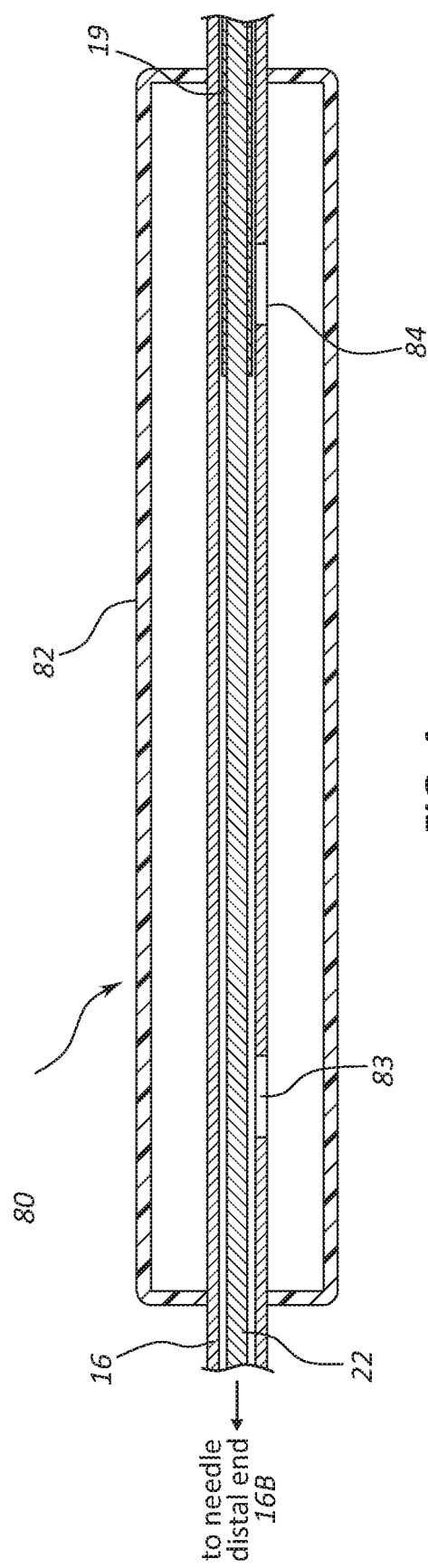
FIG. 4 is a cross-sectional side view of a blood flash indicator according to one embodiment.

Reference is now made to FIG. 4, which shows a continuous blood flash indicator 80 that can be used with the device 10 according to one embodiment. The flash indicator 80 is employed to indicate the presence of blood in the lumen of the needle 16 during use of the device 10, thus assuring that proper access has been made by the needle into a vein or other desired blood-carrying vessel. As shown, the flash indicator 80 includes a translucent chamber 82 that is generally cylindrical in shape, sealed at either end, and disposed about a portion of the needle 16 such that the needle protrudes out from either sealed end. In the present embodiment the chamber 82 is disposed just distal to the needle hub 14 within the housing 12, though other locations along the needle are also possible.

Two notches—a first notch 83 and a second notch 84—are defined in the needle 16 so as to provide fluid communication between the lumen of the needle and the interior of the chamber 82. The notches 83 and 84 replace the notch 18

(FIG. 1I) in one embodiment, and are included in addition to the notch 18, in another embodiment. It is appreciated that, in one embodiment, blood passage through the notch 18 serves as an initial indicator that the distal end 16B of the needle has entered the vein, while the embodiment shown here serves as an additional indicator to verify that the needle distal end remains in the vein after initial access.

In the present embodiment, the second notch 84 is disposed just proximal to the distal termination point of the guidewire support tube 19, though other locations for the notches are possible. Also as shown, the guidewire 22 passes through the lumen of the needle 16 so as to extend through the flash indicator 80. The first notch 83 is disposed distal to the second notch 84 toward the distal end of the chamber 82, as shown in FIG. 4.

When vessel access is achieved by the distal end 16B of the needle 16, blood travels proximally up the lumen of the needle, between the inner surface of the needle and the outer surface of the guidewire 22, disposed in the needle lumen. Upon reaching the relatively more distal first notch 83 defined in the needle 16, a portion of the blood will pass through the first notch and enter the chamber 82. As the blood fills the chamber 82, a user can observe the translucent chamber through the translucent housing 12 of the insertion device 10 and view the blood therein, thus confirming that the vessel access has been achieved. In another embodiment, the housing 12 can be configured such that direct viewing of the chamber 82 is possible, e.g., with no intervening structure interposed between the chamber and the user.

The second notch 84 is employed to provide an exit point for air in the chamber 82 to equalize air pressure and enable the blood to continue entering the chamber via the first notch 83. It is noted that the spacing between the inner surface of the needle 16 and the outer surface of the guidewire support tube 19 is such that air but not blood can pass therebetween, thus enabling air pressure equalization in the chamber 82 without blood passage through the second notch 84. In this way, the flash indicator 80 is a continuous indicator, enabling a continuous flow of blood into the chamber 82 while the needle distal end 16B is disposed within the vessel.

Note that the chamber 82 of the flash indicator 80 of the present embodiment is disposed so as to be directly under the ribs 56 of the distal portion 49 of the as-yet un-advanced advancement member 48 during the establishment of needle access to the vessel. This enables the ribs 56 to act as an indicia, or an approximate blood flash meter, as the blood proceeds proximally within the chamber 82 of the flash indicator 80; a user observing the blood in the spaces between the ribs 56 proceeding proximally can view the proximal travel of the blood during the catheter placement procedure. In another embodiment, a spring disposed in the housing 12, such as for retraction of the needle 16, can also serve as indicia to meter the flow of blood in the flash indicator. These and other indicia for metering blood flow in the flash indicator are therefore contemplated.

Note that the catheter insertion device 10 can include more than one flash indicator. In one embodiment and as mentioned above, for instance, the blood flash indicator 80 can be included, along with another flash indicator, such as the notch 18, which enables blood present in the lumen 17 of the needle 16 to proceed proximally up the space between the outer surface of the needle and the inner surface of the catheter 42.

Figure 1J:
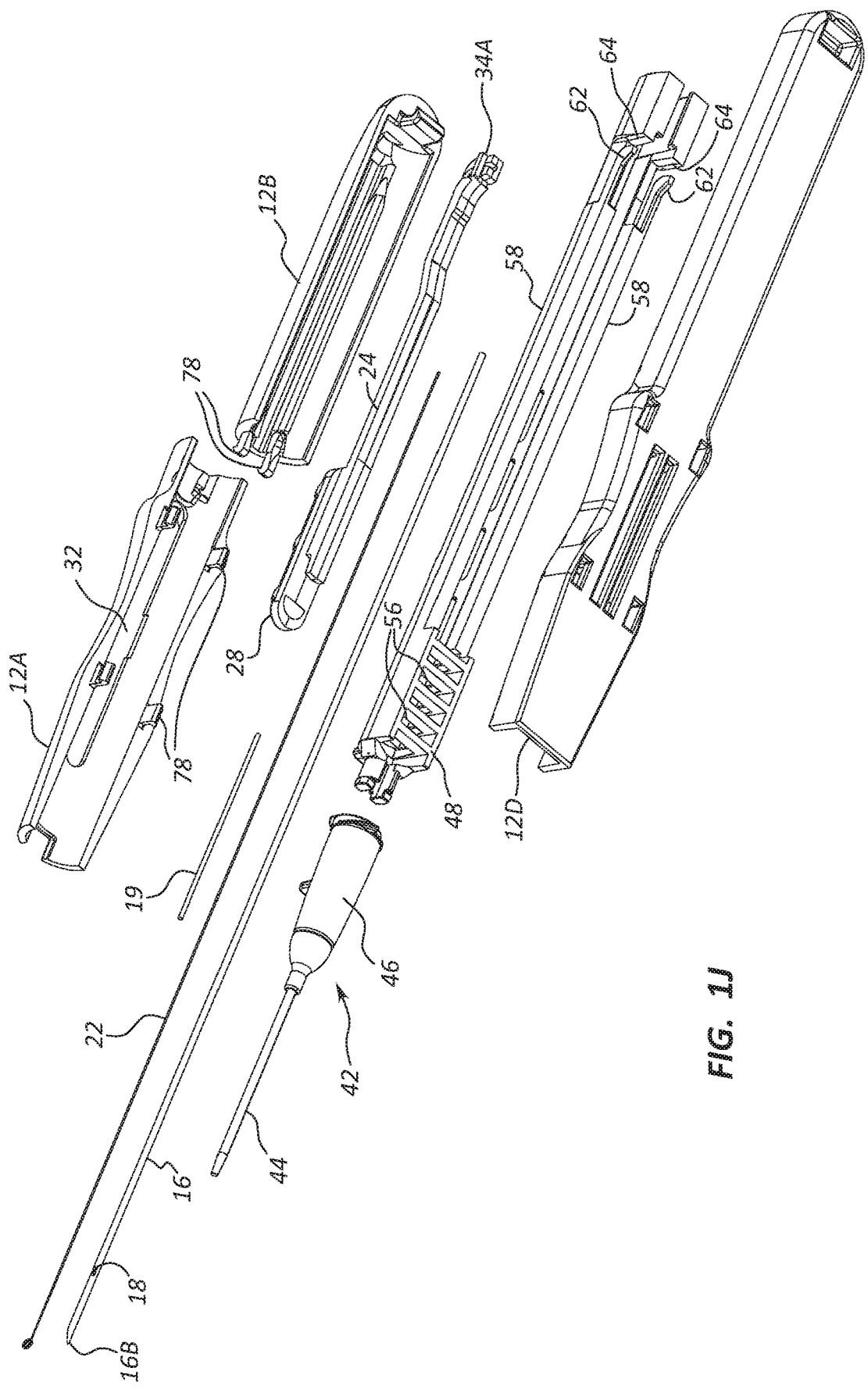
Figure 5:
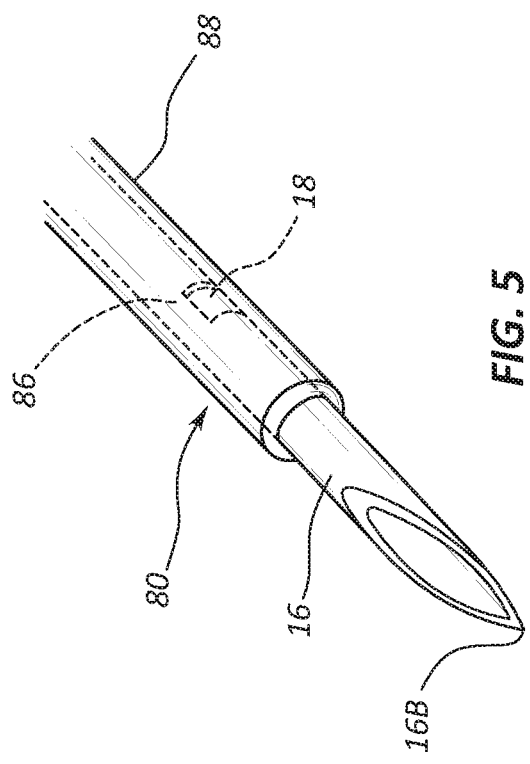
FIG. 5 is a perspective view of a blood flash indicator according to one embodiment.
Figure 6:
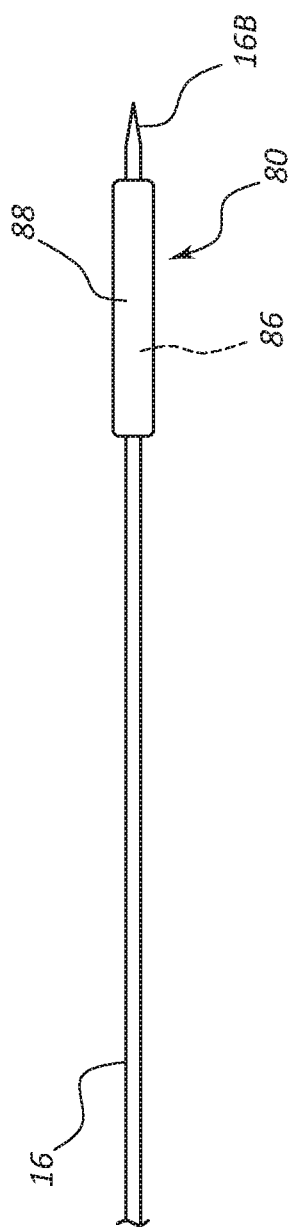
FIG. 6 is a top view of a blood flash indicator according to one embodiment.

FIGS. 5 and 6 show another example of a continuous blood flash indicator 80 according to one embodiment, wherein an absorbent component 86 capable of absorbing blood or other desired body fluid is wrapped/disposed about a portion of the outer surface of the needle 16 so as to cover the notch 18 of the needle (FIGS. 1I, 1J). Cotton, gauze, fabrics, wood-based products, hydrophilic materials, mesh materials, polymeric materials, polyester, woven materials, and other suitable substances—both natural and synthetic materials—are examples of materials that can be employed for the absorbent component. In one embodiment, the absorbent material is woven to include a weave such that the blood fills the spaces between the woven material. This enables the amount of expansion of the absorbent material as well as the speed of blood travel through the absorbent material. Note that expansion of the absorbent material can be radial, longitudinal, a combination of both, etc.

The absorbent component preferably has a color different from red so as to indicate when blood has been absorbed. A translucent cover 88, including a thermoplastic or other suitable material, can be optionally placed over the absorbent component 86 in one embodiment to contain it and isolate blood absorbed thereby.

Figure 7:
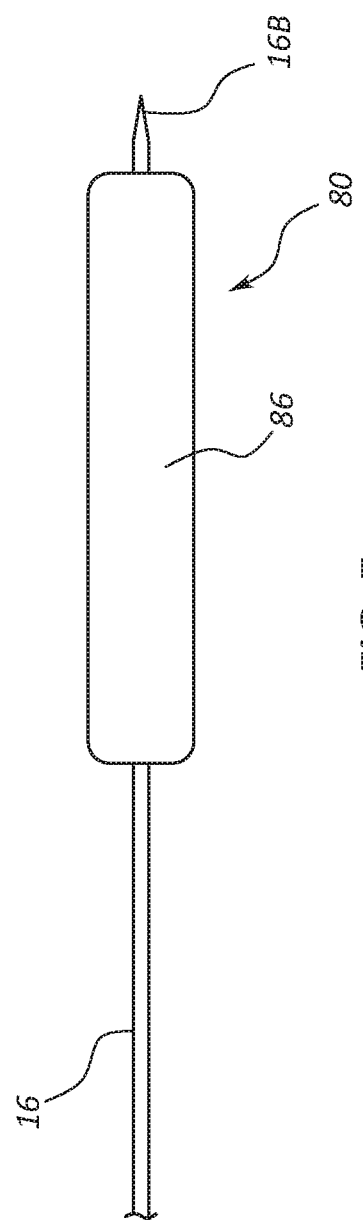
FIG. 7 is a top view of a blood flash indicator according to one embodiment.

When vessel access is achieved by the distal end 16B of the needle 16, blood travels proximally up the lumen of the needle, between the inner surface of the needle and the outer surface of the guidewire 22, which is disposed in the needle lumen. Upon reaching the notch 18 defined in the needle 16, a portion of the blood will pass through the notch and be absorbed by the absorbent component 86, which changes colors due to the blood absorption. This indicates to the user that the needle distal tip 16B is properly located in the vessel. As the needle distal tip 16B remains in the vessel, blood will continue to be absorbed by the absorbent component 86, causing the absorbed blood to progress along the length of the absorbent component, thus providing a continuous blood flash indication. FIG. 7 shows that the diameter of the absorbent component 86 can vary in size; as such, modifications to what has been shown and described herein are therefore contemplated. In another embodiment it is appreciated that the absorbent material can expand in size as it absorbs blood or other fluid with which it is to be used.

Figure 30A:
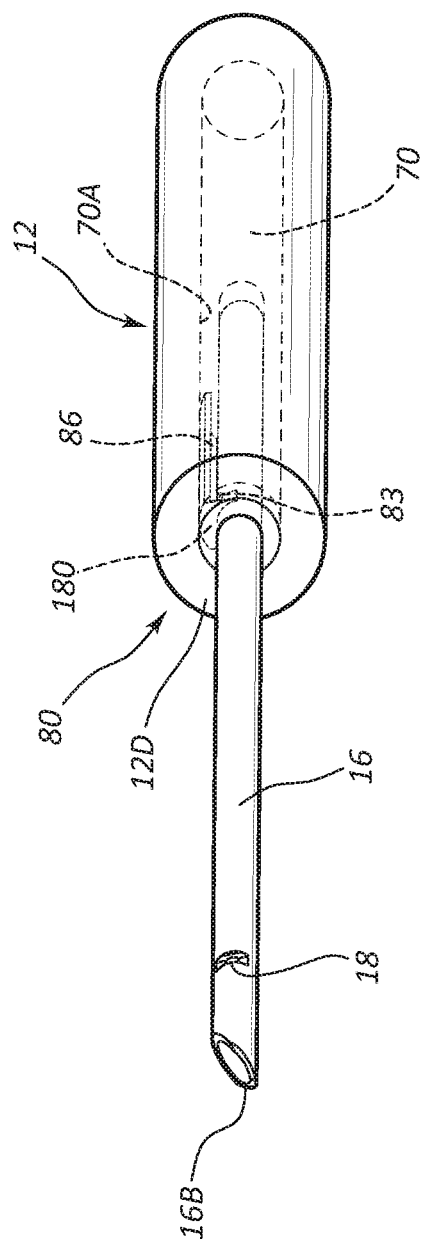
FIGS. 30A and 30B depict various views of a blood flash indicator according to one embodiment.
Figure 30B:
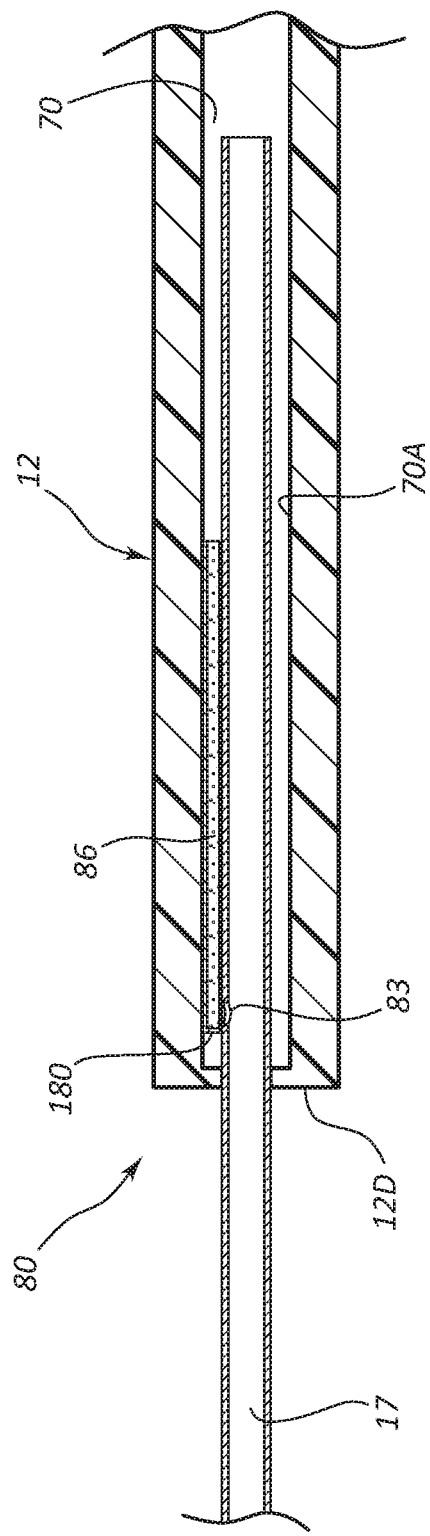

FIGS. 30A and 30B depict various details of a variation of the blood flash indicator 80 of FIGS. 5 and 6 wherein the absorbent component 86 includes a strip of absorbent material a first portion of which is disposed over a notch in the needle 16, such as the first needle notch 83. The first portion of the absorbent material strip is connected to a second portion of the absorbent material strip that longitudinally extends proximally from the first notch 83, though it may also extend in other directions and possess other shapes, sizes, etc. The second portion of the absorbent material strip is secured to an inner surface 70A of the housing cavity 70 and is connected to the first portion covering the first notch 83 via a tether 180, which also may comprise a portion of the absorbent material. So configured, the absorbent component 86 absorbs blood (or other fluid) that exits the lumen 17 of the needle 16 via the first notch 83, such as when the distal end 16B of the needle is disposed within a vein of the patient. As it continues to exit the first notch 83, the blood will be continually absorbed by the absorbent component 86 and travel from the first portion of the absorbent material, across the tether 180, and proximally along the strip of absorbent material, thus providing a continuous flash indicator to the observing user. The tether 180 is frangible in the one embodiment to enable the needle 16 to be retracted into the housing 12. Upon retracting the needle 16, the tether 180 will break, allowing the second portion of the absorbent material that is affixed to the housing cavity inner surface 70A to remain in place. In one embodiment, the flash indicator 80 described herein in connection with FIGS. 30A and 30B can be included in a flash chamber, such as the flash chamber 82 shown in FIG. 4, for instance. A variety of materials may be employed for the absorbent component, including those described in connection with FIGS. 5-7.

FIGS. 8A-8H depict details of the catheter insertion device 10 according to another embodiment, including the housing 12 from which distally extends the needle 16 secured in place by the needle hub 14 within the housing. The catheter 42 is removably disposed over the needle 16 such that the needle passes through the hub 46 and catheter tube 44, as shown. The guidewire 22 is initially disposed within the housing and the lumen of the needle 16 and is selectively advanceable.

Figure 8A:
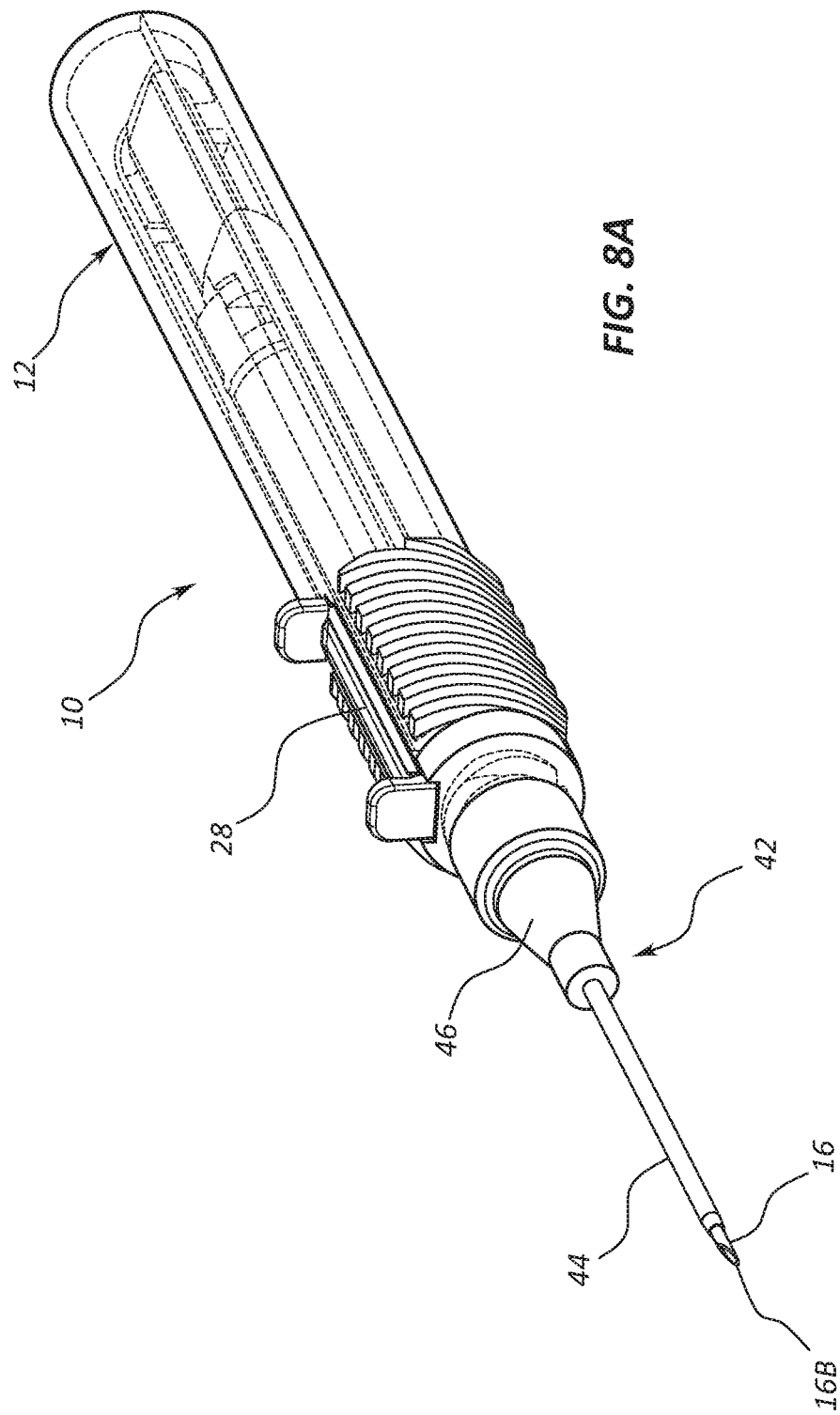
Figure 8D:
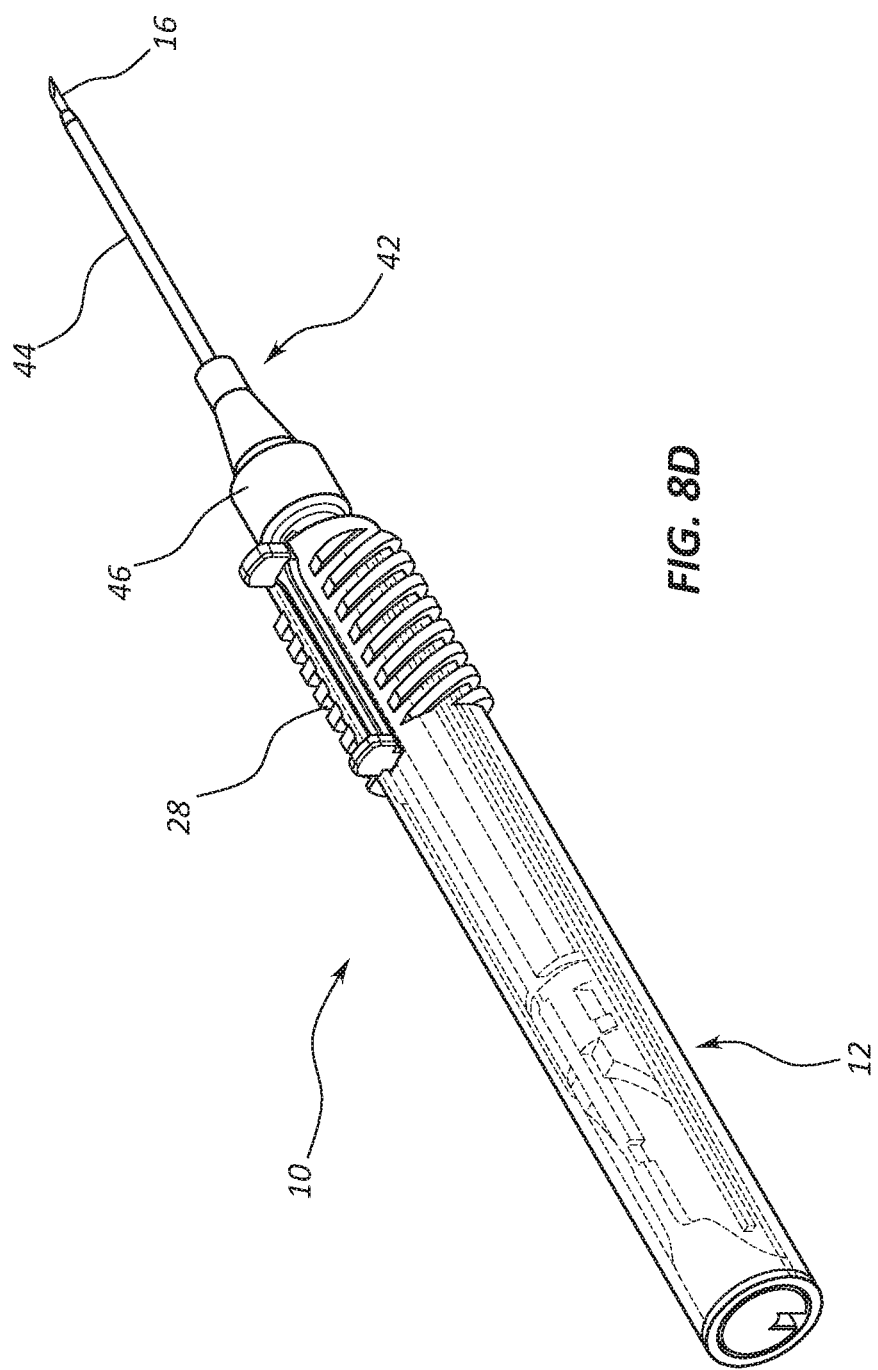

The insertion device 10 includes an advancement assembly 120 for selectively advancing the guidewire 22 and the catheter 42. The advancement assembly 120 includes the finger pad 28 that is slidably connected with the housing 12. The finger pad 28 is part of a telescoping portion 90 and can be slid distally, as shown in FIGS. 8E and 8F, to distally advance the guidewire 22 out the distal end 16B of the needle 16. Once the guidewire 22 has been fully deployed distally, further distal sliding of the finger pad 28 causes a portion of the telescoping portion 90 to engage the catheter hub 46 (FIG. 8G) and move the catheter 42 distally until the telescoping portion is fully extended (FIG. 8H). At this point, the catheter 42 can be removed from the insertion device 10, at which point the telescoping portion 90 has extended sufficient to cover and shield the distal tip 16B of the needle 16, thus protecting the user from an unintended needle stick. Operation of the insertion device 10 of FIGS. 8A-8H as described herein enables the insertion device to be used in gaining access to a vessel in the body of a patient, deploying the guidewire and catheter into the vessel, and shielding the needle 16 after use, according to one embodiment. It is noted that the embodiment shown in FIGS. 8A-8H shows one example of an insertion device that enables full guidewire and catheter advancement using a single finger pad and telescoping component.

Figure 9B:
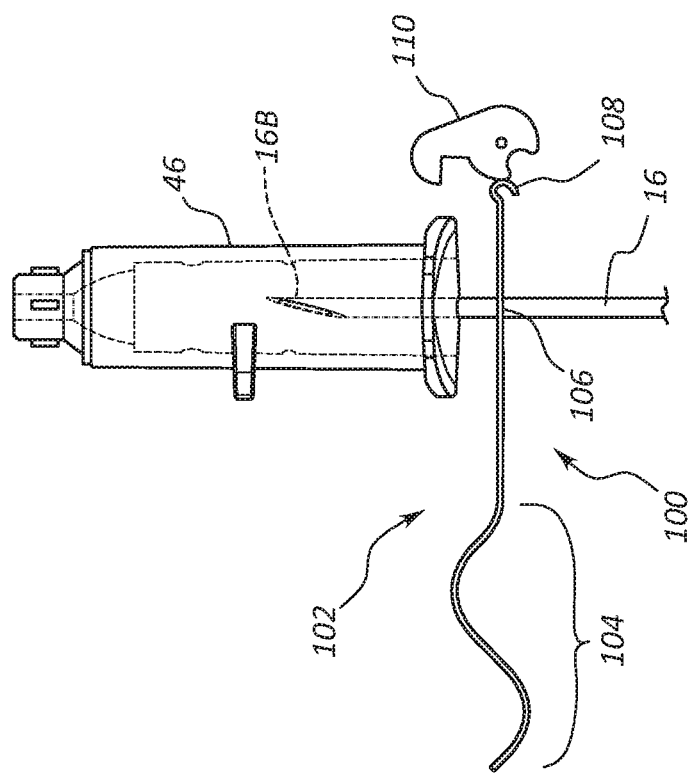
Figure 9A:
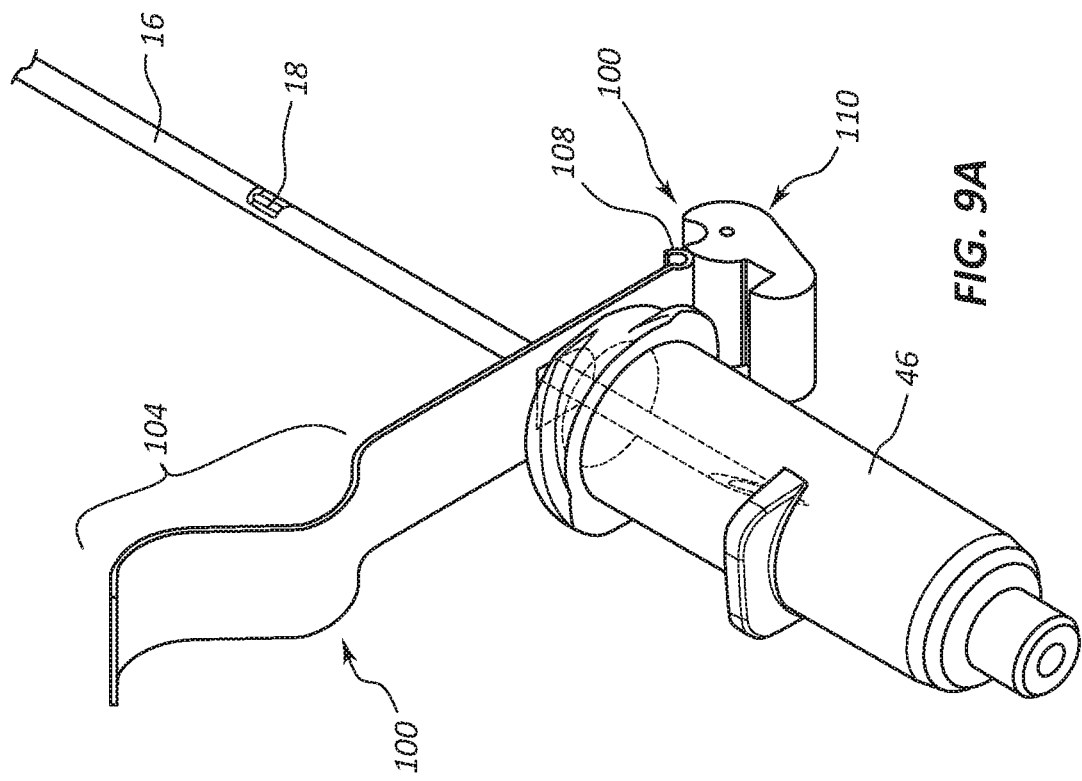
Figure 9D:
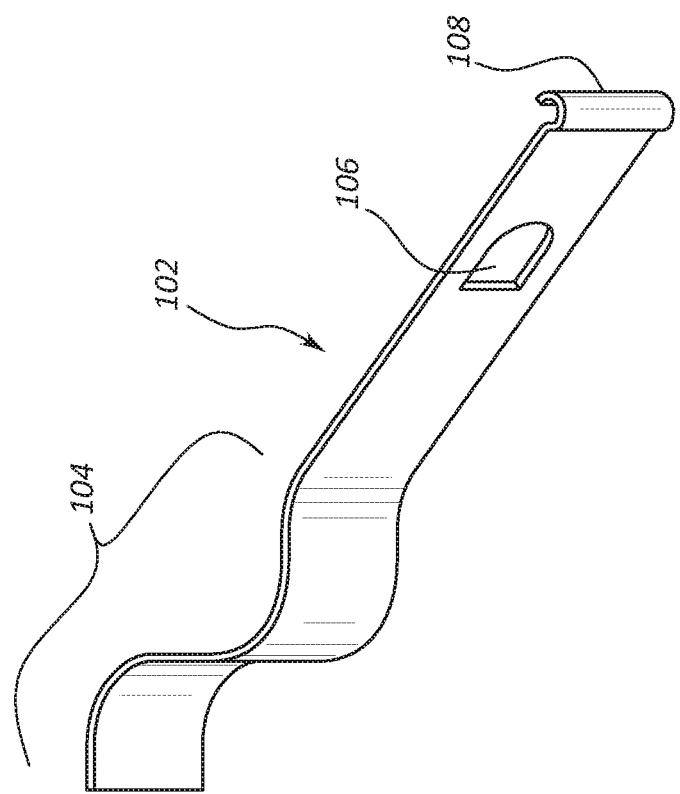
Figure 9C:
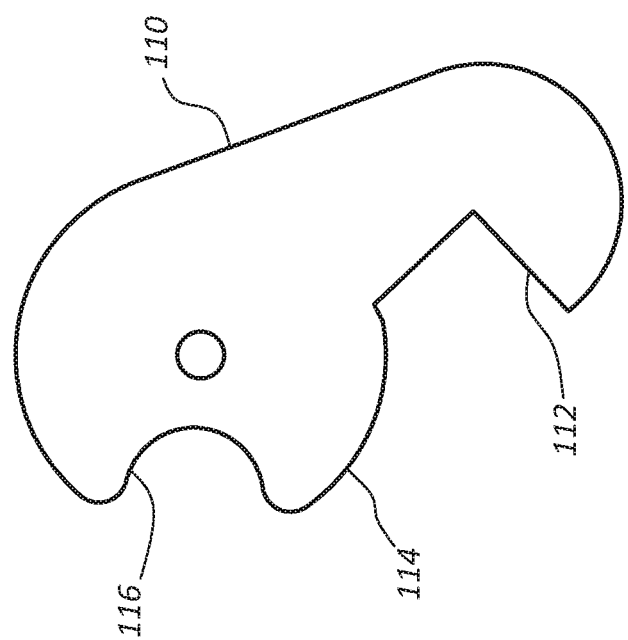
Figure 9G:
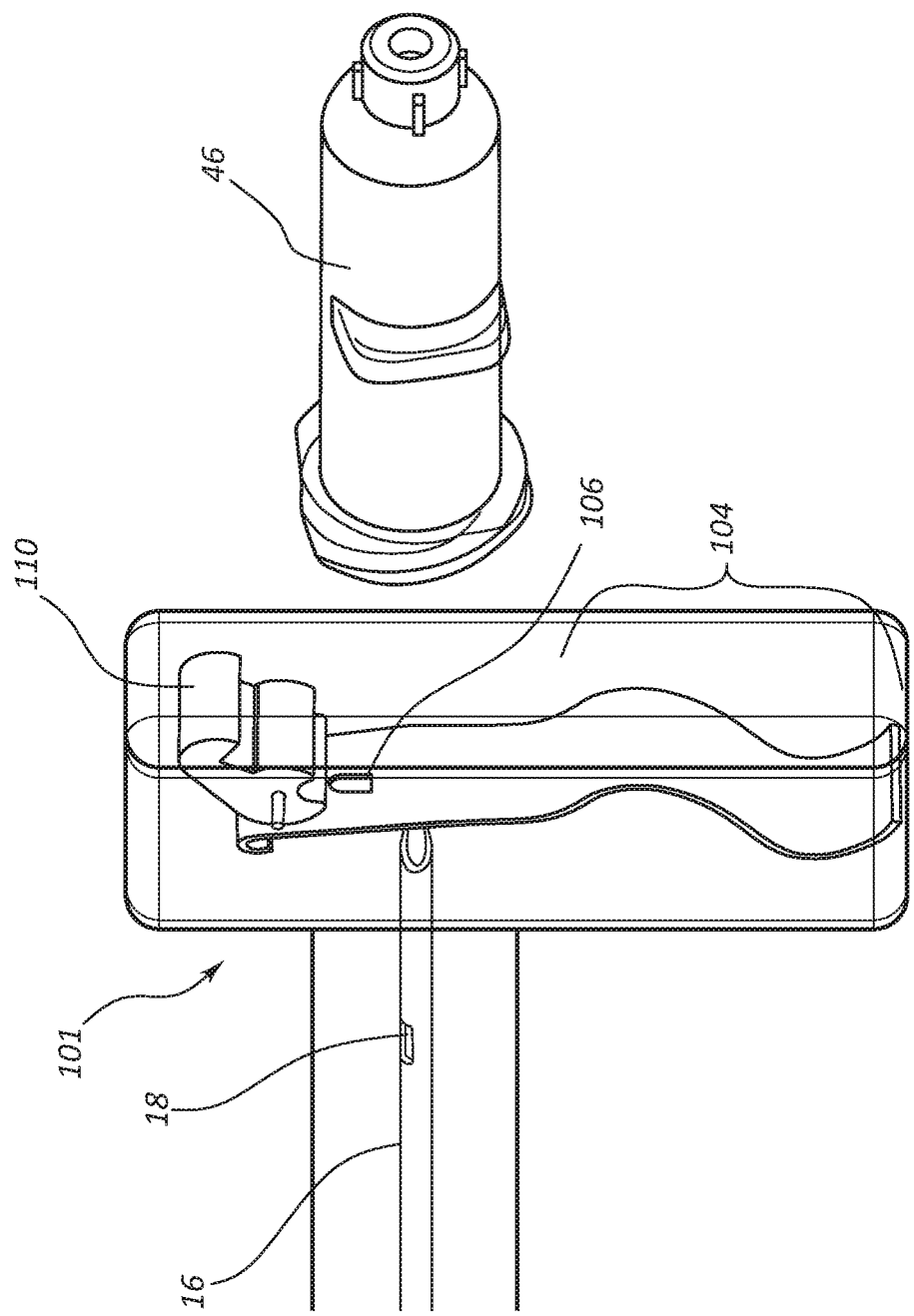

FIGS. 9A-9G depict details of a needle safety component 100 for use with a needle-bearing device, such as the insertion devices discussed herein. As shown, the needle safety component 100 is operably attached to the needle 16 and is disposed within a housing 101 (FIGS. 9E-9G). The needle safety component includes a locking element 102 that is implemented here as a flattened, elongate metal bar in which a wave-shaped spring element 104 is formed proximate one end and a hook portion 108, which acts as a cam follower, on an opposite end. A D-shaped hole 106 is defined through a central portion of the locking element 102 and the needle 16 initially passes through the hole and through the catheter 42, as shown in FIGS. 9A and 9B. Other hole shapes are also possible.

A cam 110 is rotatably within the housing 101, as shown in FIG. 9E, and includes a hub engagement portion 112, a biasing portion 114, and a locking portion 116. Before actuation, the needle safety component 100 is configured as shown in FIG. 9E, with the needle safety component disposed over the needle 16 such that the needle passes through the hole 106 and the cam 110 rotated such that the hub engagement portion 112 thereof engages a threaded portion of the hub 46 of the catheter 42 so as to maintain engagement between the catheter and the needle safety component. The biasing portion 114 of the cam 110 also engages a portion of the catheter hub 46 to help maintain engagement between the hub and the cam. Note that the spring element 104 is compressed against an interior surface of the housing 101 and the hook portion 108 of the locking element 102 is disposed in the locking portion 116 of the cam 110.

Once the catheter 42 has been positioned in the patient, the needle 16 is withdrawn from the catheter and retracted from the hole 106 in the locking element 102, while the catheter hub 46 separates from engagement with the cam 110, causing the cam to rotate counterclockwise. This rotation of the cam 110 causes the hook portion 108 of the locking element 102 to exit the locking portion 116 of the cam 110 and slide up against the side of the cam, as seen in FIG. 9F. This enables the spring element 104 to un-compress from its compressed state (shown in FIG. 9E), thus moving the hole 106 out of alignment with the needle 16 (FIG. 9G) and desirably preventing the ability of the needle to re-emerge from the housing 101. The distal tip 16B of the needle 16 is thus shielded from the user.

Figure 10:
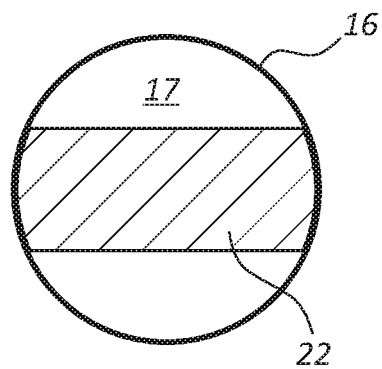
FIG. 10 is a cross-sectional view of a needle and guidewire according to one embodiment.
Figure 11:
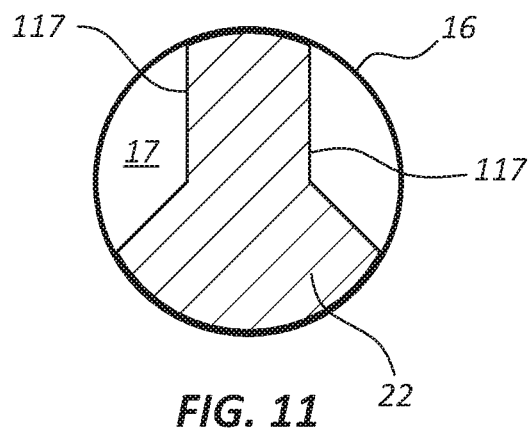
FIG. 11 is a cross-sectional view of a needle and guidewire according to one embodiment.
Figure 12:
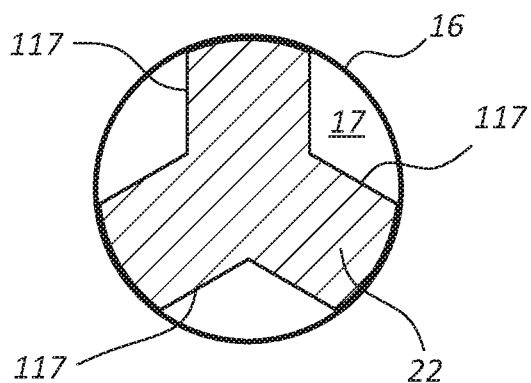
FIG. 12 is a cross-sectional view of a needle and guidewire according to one embodiment.

FIGS. 10-12 depict various examples of configurations of the guidewire 22 to enable blood to more easily pass through a lumen 17 of the needle 16, according to example embodiments. In the cross-sectional view of FIG. 10, for example, the guidewire 22 is shown disposed in a lumen 17 of the needle 16. The guidewire 22 defines a flattened bar, or generally rounded rectangular, cross-sectional shape, which frees up space within the needle lumen 17 for the passage of blood therethrough, such as when the distal tip 16B of the needle 16 enters a vein or other blood-carrying vessel of the patient. This, in turn, helps blood to flow into a blood flash indicator, such as those shown and described herein.

FIG. 11 shows a cross-sectional configuration of the guidewire 22 according to another embodiment, wherein the cross-sectional view of the guidewire depicts two longitudinal notches 117 defined in the guidewire profile. FIG. 12 shows three notches 117 defined in the cross-sectional profile of the guidewire 22. These and other guidewire configurations are therefore contemplated.

Figure 13:
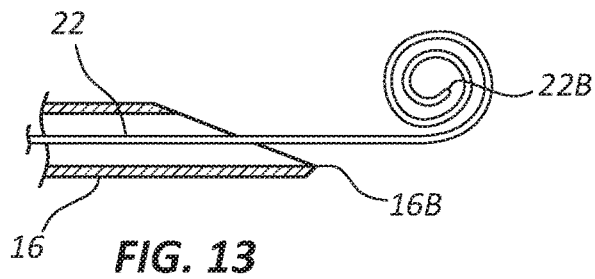
FIG. 13 is a partial cross-sectional side view of a needle and guidewire according to one embodiment.
Figure 14:
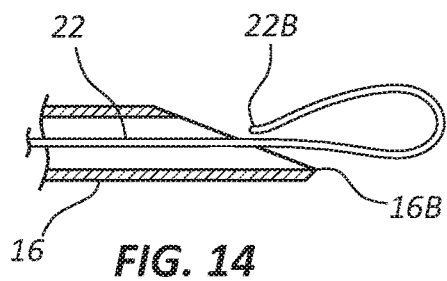
FIG. 14 is a partial cross-sectional side view of a needle and guidewire according to one embodiment.
Figure 15:
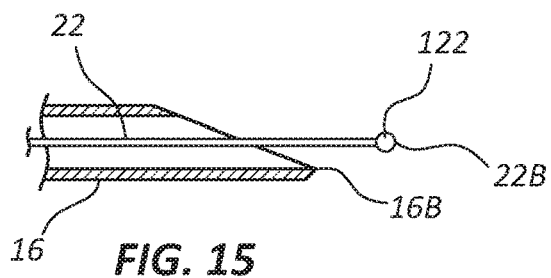
FIG. 15 is a partial cross-sectional side view of a needle and guidewire according to one embodiment.
Figure 16:
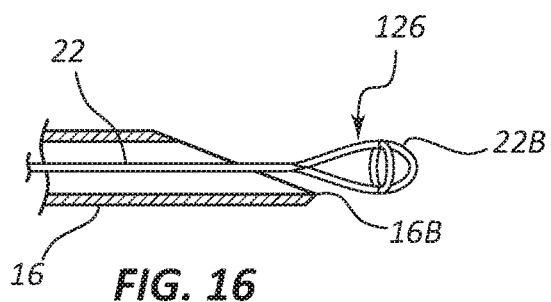
FIG. 16 is a partial cross-sectional side view of a needle and guidewire according to one embodiment.
Figure 17:
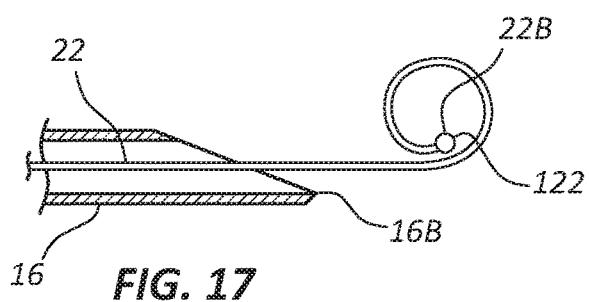
FIG. 17 is a side view of a guidewire according to one embodiment.

FIGS. 13-17 depict various examples of configurations of a distal end 22B of the guidewire 22 that are designed to provide an atraumatic tip to prevent damage to the vessel during catheter insertion procedures. For example, FIG. 13 shows the guidewire 22 extending out the distal tip 16B of the needle 16. The distal portion of the guidewire 22 includes a curled configuration proximate the distal guidewire end 22B. FIG. 14 shows a J-tipped guidewire configuration wherein the guidewire distal end 22B is doubled back on itself to form a J-tip. In FIG. 15, a thermoplastic or metallic ball 122 is secured to the distal end 22B of the guidewire 22. In FIG. 16, a three-dimensional whisk-like tip 126 is provided at the distal end 22B of the guidewire 22. FIG. 17 shows another configuration, wherein the guidewire distal end 22B includes a ball attached thereto, and the distal portion of the guidewire 22 is in a curled configuration. These and other modifications to the guidewire 22 are therefore contemplated. Note that in one embodiment, the guidewire 22 is composed of nitinol or other suitable material, as may be contemplated.

Figure 18:
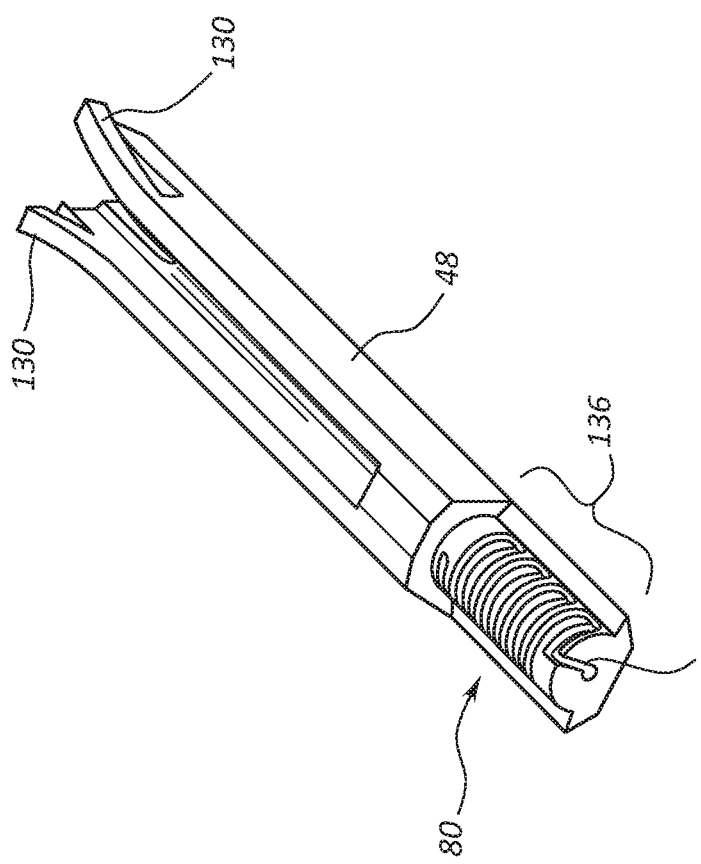
FIG. 18 is a perspective view of an advancement member of a catheter insertion tool according to one embodiment.

FIG. 18 depicts the advancement member of the catheter insertion device 10 according to another embodiment, wherein the advancement member includes outwardly-extending wings 130 on a proximal end thereof, which are configured to prevent re-entry of the advancement member into the housing of the insertion device after full extension of the advancement member has been performed. This is but one example of modes by which unintended advancement member re-entry can be prevented.

FIG. 18 further depicts a continuous blood flash indicator 80 according to one embodiment, wherein an elongate channel 134 is defined on a surface portion of the advancement member 48 so as to be in fluid communication with the lumen of the needle 16 of the insertion device 10. The channel 134 is shaped as to define a pathway 136, such as a tortuous pathway for instance, along which blood present in the lumen of the needle 16 can travel after exiting the needle. The pathway 136 shown in FIG. 18 defines a back-and-forth pattern along a top portion of a cylindrical segment of the advancement member 48, though a variety of different pathway designs can be employed. A user can observe the blood within the pathway 136 defined by the channel 134 to confirm that the distal tip of the needle 16 is disposed in the vein or other desired blood-carrying vessel of the patient. As the pathway 136 is relatively lengthy, the progress of the blood as it proceeds in the channel enables the flash indicator 80 to function as a continuous flash indicator. It is appreciated that the channel and pathway can be formed with one of a variety of processes, including molding, machining, etc.

Figure 19:
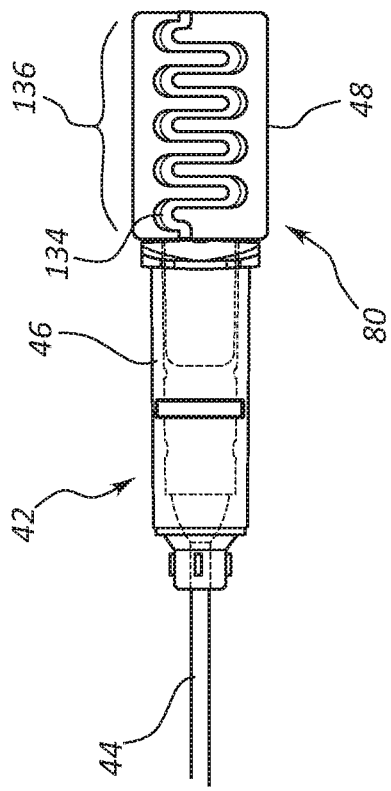
FIG. 19 is a top view of a blood flash indicator according to one embodiment.

In light of the above, FIG. 19 depicts the continuous blood flash indicator 80 according to another embodiment, wherein the channel 134 defines a wavy, back-and-forth pathway 136 on a surface of the advancement member. As before a distal end of the channel 134 is in fluid communication with the lumen of the needle of the insertion device (or other medical device) so that blood may exit the needle lumen and enter the pathway 136 defined by the channel. Though shown here as being defined on the advancement member 48 of the catheter insertion device, the channel 134 can be included on other structures, including the hub or other portion of the catheter, the housing of the catheter insertion device/medical device/component, a valve assembly, etc. Further, though shown here as defined on a surface of the advancement member, the channel in other embodiments can include at least a portion of a tunnel or pathway defined below the surface of the advancement member/medical device/component. The pathway can be covered by a translucent or other cover, in another embodiment.

Figure 22:
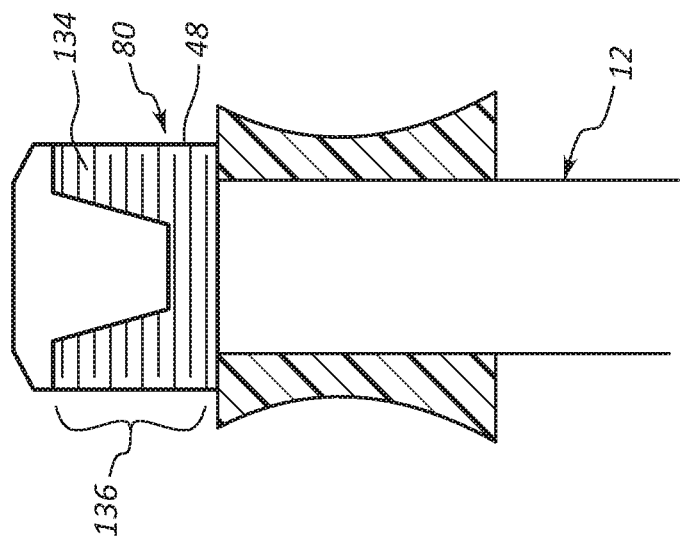
FIG. 22 is a top view of a blood flash indicator according to one embodiment.
Figure 21:
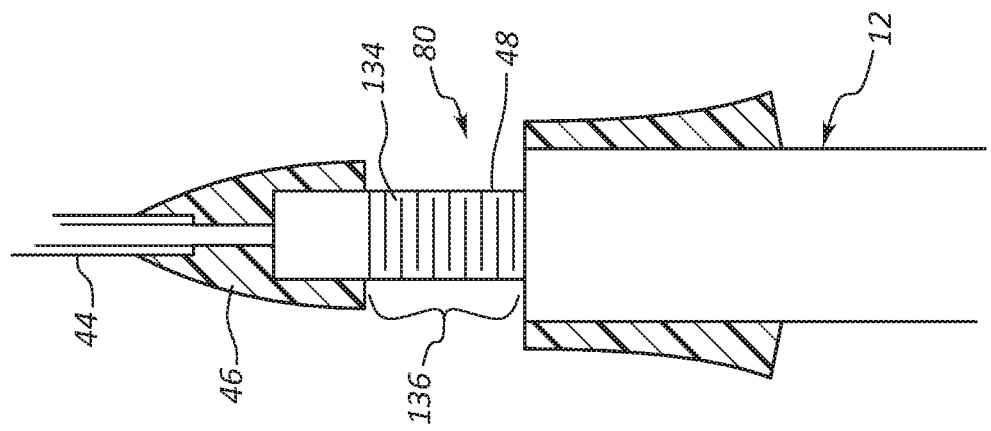
FIG. 21 is a top view of a blood flash indicator according to one embodiment.
Figure 20:
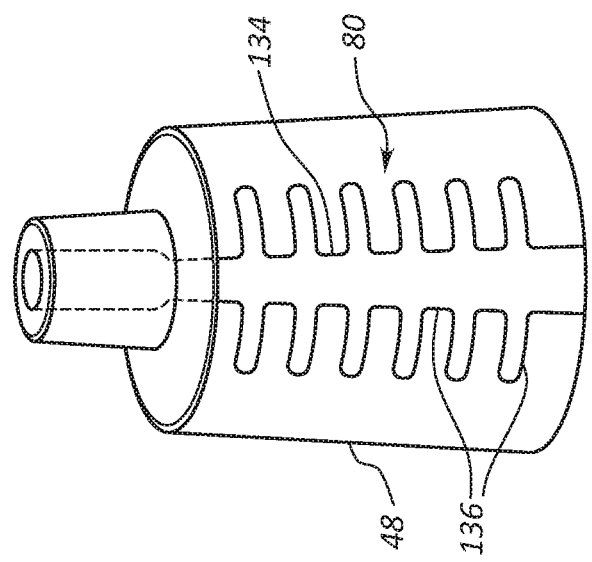
FIG. 20 is a top view of a blood flash indicator according to one embodiment.
Figure 25:
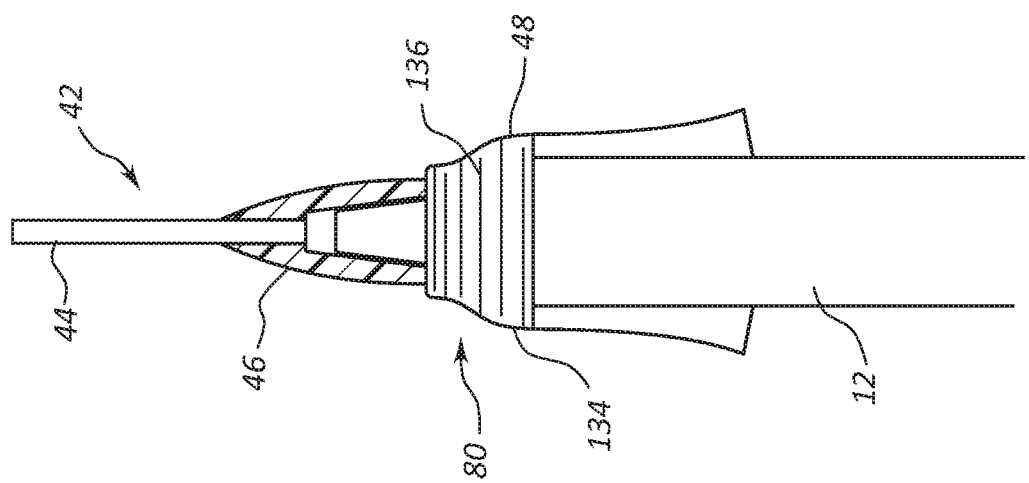
FIG. 25 is a top view of a blood flash indicator according to one embodiment.
Figure 24:
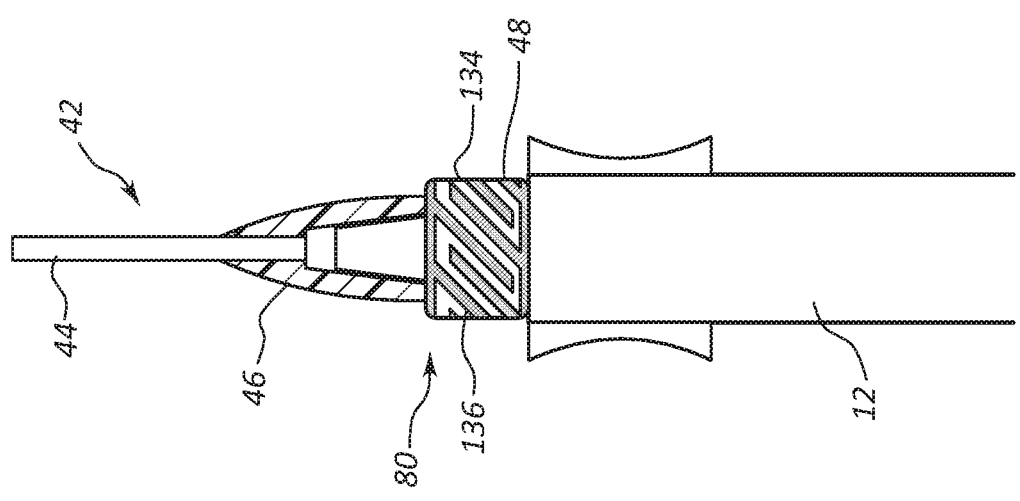
FIG. 24 is a top view of a blood flash indicator according to one embodiment.
Figure 23:
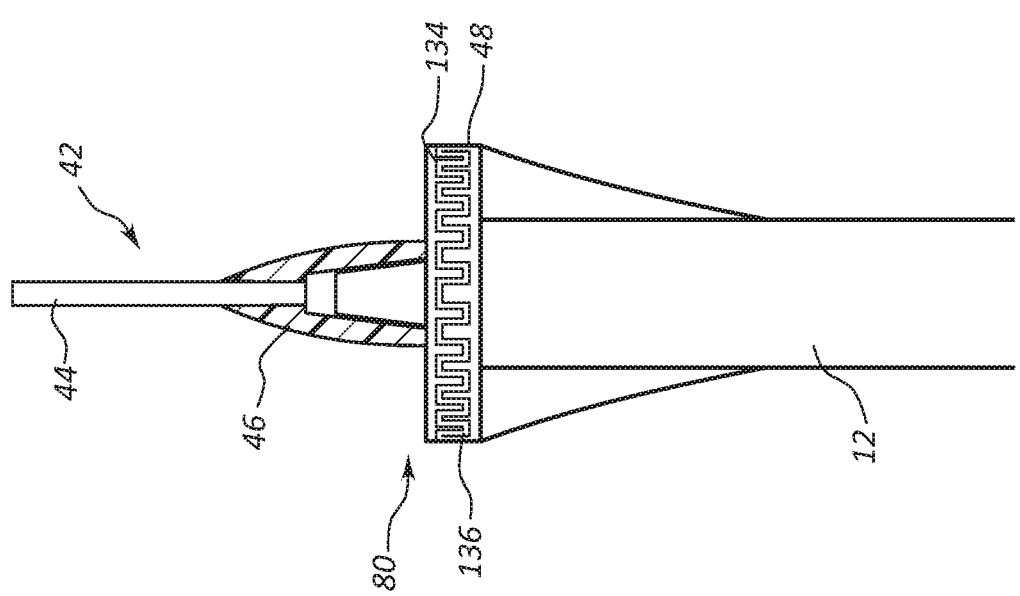
FIG. 23 is a top view of a blood flash indicator according to one embodiment.

FIG. 20 depicts the continuous blood flash indicator 80 according to another embodiment, wherein the channel 134 defines a trunk-and-branch pathway 136. In FIGS. 21 and 22, the advancement member 48 includes the channel 134 defining a back-and-forth pathway 136 on a relatively thin distal portion (FIG. 21) and a relatively thick portion (FIG. 22) of the advancement member. FIG. 23 depicts the channel 134 as defining a tooth-like pathway 136 about a circumference of a distal portion of the advancement member 48, while FIG. 24 shows the channel defining an angled zig-zag pattern thereon. And in FIG. 25, the channel 134 defines a converging back-and-forth pathway. Thus, these and other pathway designs, including circular, helix, etc., are contemplated.

It is appreciated that various other configurations are contemplated for the continuous blood flash indicator 80 and its shaped pathway. For instance, the flash indicator can be included on/with the catheter hub 46 such that blood travels through the lumen 17 of the needle 16 to the catheter hub and into the flash indicator. In yet another embodiment, the flash indicator 80 is included as a removable piece temporarily attached to the catheter hub 46 or other component of the insertion device 10. It is further appreciated that the flash indicators described herein can also be used to indicate the presence of other fluids in the needle, including other bodily fluids, for instance. These and other modifications are contemplated.

FIGS. 26A-26D depict details of the catheter insertion device 10 according to another embodiment, wherein the housing 12 has been removed from the views in FIGS. 26A-26C for clarity. The insertion device 10 here includes the needle 16 distally extending from the housing 12, with the catheter 42 removably disposed over the needle such that the needle passes through the hub 46 and catheter tube 44. The guidewire 22 is initially disposed within the housing and the lumen of the needle 16, and is selectively advanceable.

The insertion device 10 includes the advancement assembly 120 for selectively advancing the guidewire 22 and the catheter 42. The advancement assembly 120 includes an advancement slide 140, which in turn includes a finger pad 148 that is slidably connected with the housing 12. A guidewire carriage 124 is also included, from which distally extends the guidewire 22 to enter the needle 16. An end piece 158 is also included at the distal end of the housing 12 and serves to push the catheter 42 distally, as will be discussed.

The initial position of the catheter insertion device 10 is shown in FIG. 26A (excluding the omitted housing 12, for clarity), wherein the advancement slide 140 and the guidewire carriage 124 are coupled together, as shown in FIG. 26C. In detail, an arm 152 distally extending from the guidewire carriage 124 couples with an angled tab 150 of the advancement slide 140 via a notch 154 defined by the arm. Note that the arm 154 is downwardly biased, which would cause the arm to disengage the notch 154 from the angled tab 150; however, the housing 12 is shaped in the position shown in 26A to constrain the arm to maintain engagement with the angled tab.

The above configuration enables joint distal movement of the advancement slide 120 and the guidewire carriage 124 when the uses manually engages the finger pad 148 and slides the advancement slide distally to the position shown in FIG. 26B. This movement causes the guidewire 22 to fully extend out the distal end 16B of the needle 16, as with other embodiments. At this point, the notch 154 of the downwardly-biased arm 152 disengages with the angled tab 150 due to the arm 152 no longer being constrained by the housing 12 (or other suitable structure) to maintain the engagement with the angled tab. Thus, further distal movement of the guidewire 22 by the guidewire carriage 124 is prevented. A locking mechanism can be included to lock the guidewire carriage 124 in place, in one embodiment. Reversing the process by proximally sliding the advancement slide 120 causes the guidewire carriage 124 to re-couple with the advancement slide via re-coupling of the notch 154 of the arm 152 with the angled tab 150.

Next, further distal sliding of the advancement slide 120 via the finger pad 148 causes the advancement slide to engage the end piece 158, which in turn distally advances the catheter 42 off the needle 16 and into the patient, as desired. Once fully distally extended, the advancement slide 140 shields the distal tip 16B of the needle 16, thus protecting the user. This embodiment thus shows an example of an insertion device that enables full guidewire and catheter advancement using a single advancement assembly.

FIGS. 27A-27E depict details of the catheter insertion device 10 according to another embodiment, wherein a top portion of the housing 12 has been removed for clarity. The insertion device 10 here includes the needle 16 distally extending from the housing 12, with the catheter 42 removably disposed over the needle such that the needle passes through the hub 46 and catheter tube 44. The guidewire 22 is initially disposed within the housing and the lumen of the needle 16, and is selectively advanceable.

The insertion device 10 includes the advancement assembly 120 for selectively advancing the guidewire 22 and the catheter 42. The advancement assembly 120 includes a guidewire lever, which in turn includes the finger pad 148 that is slidable along a portion of the length of the insertion device housing 12. Two grips 162 are disposed proximate the distal end of the insertion device 10 to assist with user grasping of the insertion device.

The insertion device 10 further includes a catheter slide 168 that is distally slidable within the housing 12 to distally advance the catheter 42 during use of the insertion device for catheter insertion procedures. The catheter slide 168 includes a pair of wings 166 that interact with the guidewire lever 144 to enable catheter advancement after the guidewire 22 has been fully advanced.

Figure 27C:
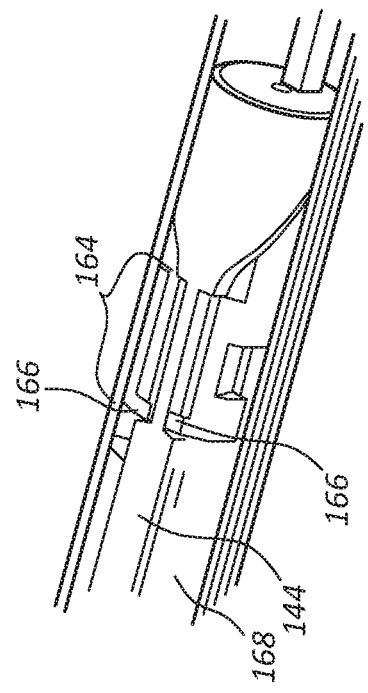
Figure 27D:
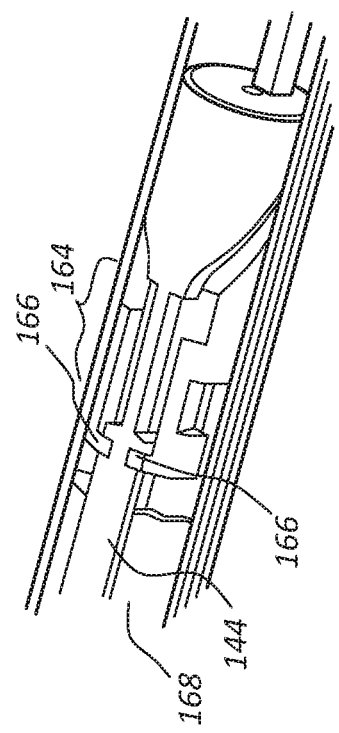
Figure 27E:
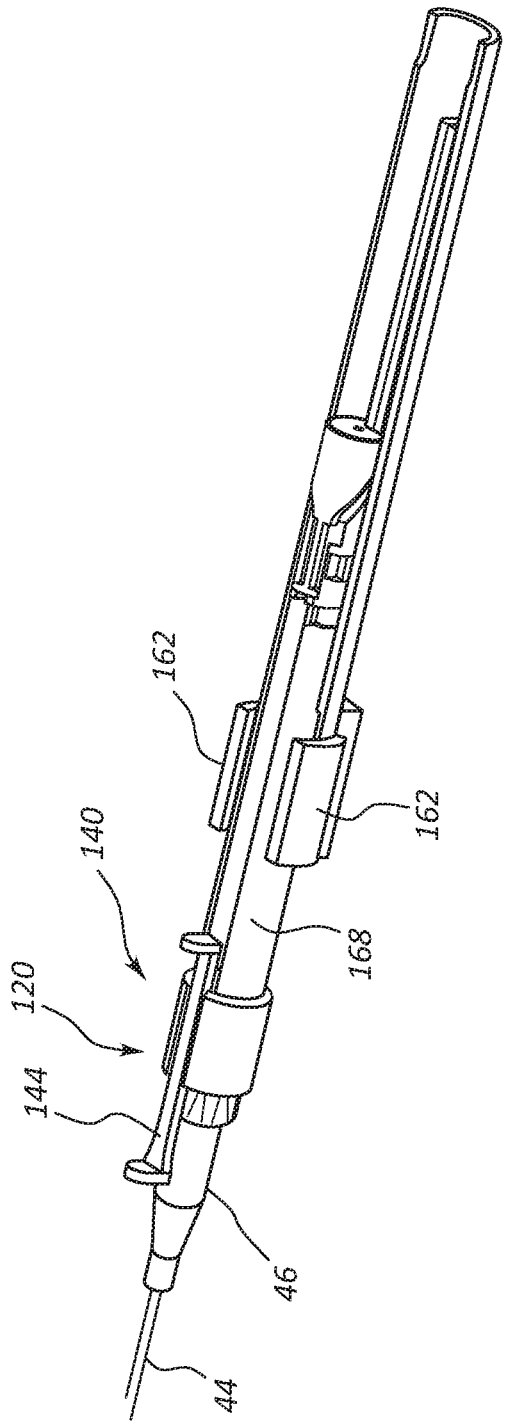

The initial position of the catheter insertion device 10 is shown in FIG. 27A (excluding the omitted top housing portion of the housing 12, for clarity), wherein the guidewire lever 144 and its finger pad 148 have not yet been distally advanced. Distal sliding of the finger pad 148 manually by the user causes the guidewire lever 144 to distally advance the guidewire 22 out the distal end 16B of the needle 16, as with other embodiments. Once the guidewire 22 has been fully extended, a thinned portion 164 of the guidewire lever 144 is now positioned adjacent the wings 166 of the catheter slide 168, as seen in FIG. 27B. So positioned, the thinned portion 164 of the guidewire lever 144 enables the wings 166—which until this point were forced radially outward by the guidewire lever (FIG. 27C)—to contract radially inward (FIG. 27D) so as to enable the catheter slide 168 to be distally advanced by further distal sliding movement by the finger pad 148 of the guidewire lever, as seen in FIG. 27E. This distal advancement of the catheter slide 168 causes the catheter 42 to be distally advanced off the needle 16 and into the patient, as desired. This embodiment thus shows another example of an insertion device that enables full guidewire and catheter advancement using a single advancement assembly.

Figure 28:
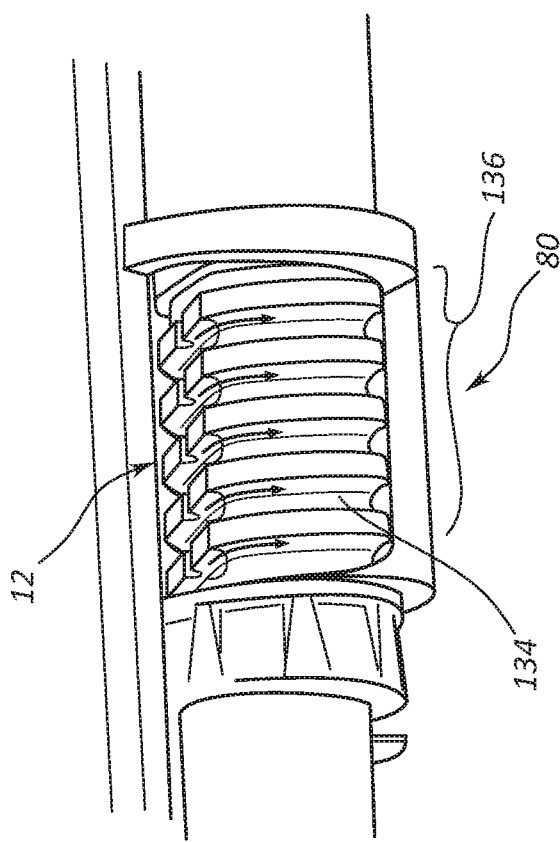
FIG. 28 is a perspective view of a blood flash indicator according to one embodiment.

FIG. 28 depicts the continuous blood flash indicator 80 of the catheter insertion device 10 shown in FIGS. 27A-27E, including the channel 134 defining the pathway 136 implemented as a spiral disposed within the housing 12 about a distal portion of the advancement assembly 120.

Figure 29:
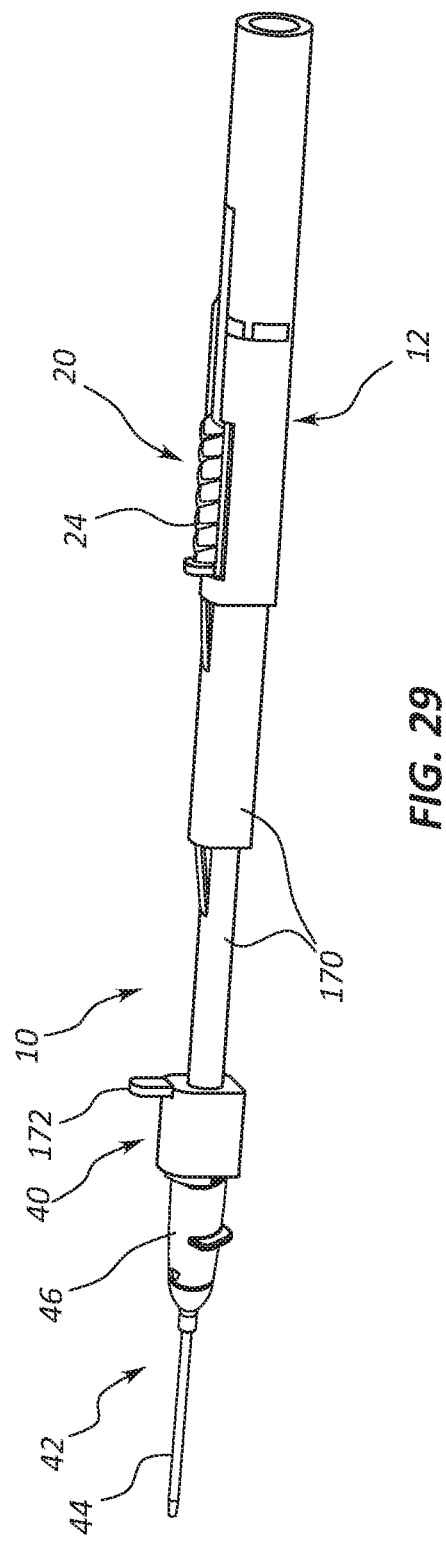
FIG. 29 is a perspective view of a catheter insertion tool according to one embodiment.

FIG. 29 depicts details of the catheter insertion device 10 according to another embodiment, including separately deployable assemblies, i.e., the guidewire advancement assembly 20 including the guidewire lever 24, and the catheter advancement assembly 40 including a tab 172 and a plurality of telescoping segments 170. During use of the insertion device 10, the guidewire 22 is distally extended manually via the guidewire lever 24, after which the catheter 42 is distally extended manually via the catheter advancement assembly 40 and the included tab 172. The telescoping segments 170 maintain attachment of the catheter advancement assembly 40 with the housing 12 and also help shield the needle from unintended user contact. Note that, though two are shown here, one, three or more telescoping segments 170 can be employed. This embodiment thus shows an example of an insertion device that enables full guidewire and catheter advancement using a separate advancement assembly for the guidewire and the catheter.

It is noted generally that, in one embodiment, the advancement assembly/assemblies can be configured to prevent distal advancement of the catheter until full distal advancement of the guidewire has been achieved. In other embodiments, a single advancement assembly is employed to advance both the guidewire and the catheter. For instance, the finger pad of an advancement assembly can be moved a first distance to distally advance the guidewire, after which further guidewire advancement is automatically or otherwise disengaged/prevented and the catheter distal advancement is commenced as the finger pad is moved a second distance, as in FIGS. 26A-26D. In another embodiment, a single finger pad is moved a first distance to distally advance the guidewire, then moved a second distance to continue moving the guidewire distally while also now moving the catheter distally as well, such as in FIGS. 27A-27E. These and other possible configurations are contemplated.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An insertion device for inserting a catheter into a body of a patient, the catheter including a catheter hub, the insertion device comprising:
   a housing;
   an at least partially hollow needle distally extending from the housing, at least a portion of the catheter pre-disposed over the needle such that the catheter hub is disposed substantially external to the housing;
   a guidewire including a distal end pre-disposed in a lumen of the needle; and
   an advancement assembly configured to selectively advance the distal end of the guidewire out a distal opening of the needle and to selectively advance the catheter and catheter hub over the needle, wherein:
   the insertion device is configured to be operated by a single hand of a user,
   the advancement assembly is configured to be operated without removing the single hand from the insertion device; and
   the advancement assembly includes a portion configured for insertion in the catheter hub to engage the catheter.

2. The insertion device as defined in claim 1, wherein the advancement assembly includes a finger pad movable by the user to advance at least one of the guidewire and the catheter.

3. The insertion device as defined in claim 2, wherein the finger pad is slidably disposed with the housing.

4. The insertion device as defined in claim 3, wherein the finger pad is moved a first distance to extend the guidewire out the distal opening of the needle, and wherein the finger pad is moved a second distance, subsequent to moving the first distance, to extend the catheter in a distal direction.

5. The insertion device as defined in claim 4, wherein an advancement member is moved by the finger pad when the finger pad is moved the second distance, the catheter removably attached to the advancement member.

6. The insertion device as defined in claim 1, wherein the advancement assembly includes a first member used to advance the guidewire and a second member used to advance the catheter, and wherein the user is readily able to move from the first member to the second member without substantial repositioning of the single hand.

7. The insertion device as defined in claim 6, wherein the first member is distally slidable to a distal termination point that is proximate a proximal commencement point of the second member.

8. The insertion device as defined in claim 1, wherein the advancement assembly is moved a first distance to extend the guidewire out the distal opening of the needle, and wherein the advancement assembly is moved a second distance, subsequent to moving the first distance, to extend the catheter in a distal direction.

9. The insertion device as defined in claim 8, wherein movement of the advancement assembly the second distance moves the catheter into an initial position, and subsequent action by the user moves the catheter into a final position.

10. The insertion device as defined in claim 8, wherein further advancement of the guidewire is prevented after movement of the advancement assembly the first distance.

11. The insertion device as defined in claim 8, wherein movement of the advancement assembly the second distance results in full distal advancement of the catheter.

12. The insertion device as defined in claim 1, wherein the advancement assembly includes a guidewire advancement assembly and a catheter advancement assembly.

13. The insertion device as defined in claim 12, wherein the guidewire advancement assembly is configured to distally advance only the guidewire.

14. The insertion device as defined in claim 1, wherein the advancement assembly includes a telescoping portion that extends from the housing when the catheter is advanced in a distal direction.

15. The insertion device as defined in claim 1, wherein the advancement assembly further includes a needle safety component configured to shield a distal tip of the needle after use of the insertion device.

16. The insertion device as defined in claim 1, wherein at least a portion of the guidewire includes a generally rounded rectangular cross-sectional profile.

17. The insertion device as defined in claim 1, wherein the guidewire includes a cross-sectional profile defining first and second notches that are longitudinally defined along at least a portion of a length of the guidewire.

18. The insertion device as defined in claim 1, wherein the guidewire includes a cross-sectional profile defining first, second, and third notches that are longitudinally defined along at least a portion of a length of the guidewire.

19. The insertion device as defined in claim 1, further including a continuous blood flash indicator configured to alert the user when blood is present in the lumen of the needle.

20. An insertion device for inserting a catheter into a body of a patient, the catheter including a catheter hub, the insertion device comprising:
a housing;
a hollow needle distally extending from the housing, at least a portion of the catheter pre-disposed over the needle such that the catheter hub is disposed substantially external to the housing;
a guidewire including a distal end pre-disposed in a lumen of the needle;
a guidewire advancement assembly including a guidewire lever configured to selectively advance the distal end of the guidewire out a distal end of the needle; and
a catheter advancement assembly configured to selectively advance the catheter over the needle, wherein:
the catheter advancement assembly and the guidewire advancement assembly are operable by a single hand of a user without removing the single hand from the insertion device, and
the catheter advancement assembly covers the distal end of the needle following detachment of the catheter from the catheter advancement assembly.

21. The insertion device as defined in claim 20, wherein the guidewire lever of the guidewire advancement assembly includes a finger pad movable by the user to advance the guidewire.

22. The insertion device as defined in claim 21, wherein the finger pad is slidably disposed with the housing.

23. The insertion device as defined in claim 22, wherein the finger pad is moved a first distance to cause the guidewire lever to extend the guidewire out a distal opening of the needle, and wherein the finger pad is moved a second distance, subsequent to moving the first distance, to cause the guidewire lever to extend the catheter in a distal direction.

24. The insertion device as defined in claim 23, wherein an advancement member is moved distally by the guidewire lever when the finger pad is moved the second distance, the advancement member initially substantially disposed within the housing prior to movement, the catheter removably attached to the advancement member.

25. The insertion device as defined in claim 24, wherein distal movement of the advancement member moves the catheter into an initial position, and subsequent action by the user moves the catheter into a final position.

26. The insertion device as defined in claim 25, wherein at least one tab is included on the advancement member to enable manual advancement by the user of the advancement member.

27. The insertion device as defined in claim 26, wherein the advancement member includes a distal portion, the distal portion including first and second engagement tabs configured to releasably constrain the catheter in place over the needle before advancement of the advancement member, the needle initially disposed between the engagement tabs to cause the engagement tabs to engage the catheter, wherein the engagement tabs release from engagement with the catheter after the advancement member has been distally advanced past the distal end of the needle such that the needle is no longer disposed between the engagement tabs.

28. The insertion device as defined in claim 27, wherein the advancement member is configured to shield the distal end of the needle after the advancement member has been fully distally advanced.

29. The insertion device as defined in claim 28, wherein the advancement member includes one or more locking tabs that engage with a portion of the housing after full distal advancement of the advancement member to prevent re-entry of the advancement member into the housing.

30. The insertion device as defined in claim 29, further including a continuous blood flash indicator configured to alert the user when blood is present in the lumen of the needle, comprising:
a first notch defined in a side wall of the needle to enable blood to pass therethrough from a lumen of the needle when the distal end of the needle is disposed in a blood-carrying vessel of the patient; and
a flash indicator configured to indicate the presence of blood within the lumen of the needle, the flash indicator including a translucent flash chamber disposed about the needle so as to enclose the first notch and configured such that blood present in the lumen of the needle passes from the lumen of the needle via the first notch to the flash chamber so as to be observable to a user of the insertion device.

31. The insertion device as defined in claim 30, wherein the flash chamber is sealed about the needle.

32. The insertion device as defined in claim 31, further comprising a second notch enclosed by the flash chamber, the second notch configured to enable blood present in the flash chamber to re-enter the lumen of the needle.

33. The insertion device as defined in claim 32, wherein the insertion device includes indicia configured to meter a quantity of blood disposed in the flash chamber.

34. The insertion device as defined in claim 33, wherein the indicia include a plurality of ribs that span a distal portion of the advancement member in proximity to the flash chamber, the blood disposed in the flash chamber observable by the user through the plurality of ribs.

35. The insertion device as defined in claim 34, wherein the guidewire includes a proximal end secured to a portion of the housing, a distal end pre-disposed within the needle, and an intermediate portion substantially defining a U-shaped bend.

36. The insertion device as defined in claim 35, wherein the distal end of the guidewire includes an atraumatic feature including at least one of a J-tip, an attached ball, a whisk structure, and a curled configuration.

37. The insertion device as defined in claim 20, wherein the guidewire advancement assembly is configured to prevent advancement of the catheter until distal advancement of the guidewire is performed.

38. The insertion device as defined in claim 20, wherein the needle is secured within the housing by a needle hub, the needle hub integrally formed with the housing, the needle hub including a pocket configured to received therein an adhesive so as to secure the needle in the needle hub.

39. The insertion device as defined in claim 20, wherein the catheter advancement assembly includes a plurality of outwardly extending wings configured to prevent re-entry of the catheter advancement member into the housing after distal advancement of the catheter.

\* \* \* \* \*